United States Patent
Rothenberg et al.

(10) Patent No.: US 6,509,442 B1
(45) Date of Patent: Jan. 21, 2003

(54) MUTATIONS ASSOCIATED WITH IRON DISORDERS

(76) Inventors: Barry E. Rothenberg, 149 12th St., Del Mar, CA (US) 92014; Ritsuko Sawada-Hirai, 13539 Jadestone Way, San Diego, CA (US) 92130; James C. Barton, 3828 Brook Hollow La., Birmingham, AL (US) 35209

( * ) Notice: Subject to any disclaimer, the term of this patent is extended or adjusted under 35 U.S.C. 154(b) by 31 days.

(21) Appl. No.: 09/679,729

(22) Filed: Oct. 4, 2000

Related U.S. Application Data

(62) Division of application No. 09/277,457, filed on Mar. 26, 1999, now Pat. No. 6,355,425.

(51) Int. Cl.⁷ .......................... C12Q 1/68; A01N 37/18; A61K 38/00; C07K 1/00

(52) U.S. Cl. ............... 530/300; 435/6; 514/2; 530/350

(58) Field of Search ............... 435/6; 530/300, 530/350; 514/2

(56) References Cited

U.S. PATENT DOCUMENTS

| | | |
|---|---|---|
| 4,946,778 A | 8/1990 | Ladner et al. |
| 5,705,343 A | 1/1998 | Drayna et al. |
| 5,712,098 A | 1/1998 | Tsuchihashi et al. |
| 5,877,015 A | 3/1999 | Hardy et al. |
| 5,879,892 A | 3/1999 | Van Baren et al. |
| 5,879,904 A | 3/1999 | Brechot et al. |
| 5,879,908 A | 3/1999 | Laping et al. |

FOREIGN PATENT DOCUMENTS

| | | | |
|---|---|---|---|
| WO | WO 98/14466 | 4/1998 | ........... C07H/21/04 |

OTHER PUBLICATIONS

Beutler, et al., "HLA–H and Associated Proteins in Patients with Hemochromatosis" *Mol. Med.*, vol. 3, No. 6, pp. 397–402 (Jun. 1997).
Douabin et al., "Polymorphisms in the HFE Gene" *Hum. Hered.*, vol. 49, No. 1, pp. 21–26 (Jan. 1999).
Sosnowski et al., Rapids determination of single base mismatch mutations in DNA hybrids by direct electic field control, Proc. Natl. Acad. Sci. USA, vol. 94, pp. 1119–1123, Feb. 1997.
Edman et al., Electic Field directed nucleic acid hybridization on microchips, Nucleic Acids Research, 1997, vol. 25, No. 24, pp. 4907–4914.
Cheng et al., Prepartion and hybridization analysis of DNA/RNA from *E. coli* on microfabricated bioelectric chips, Nature Biotechnology, vol. 16, pp. 541–546, Jun. 1998.
Lebron et al., "Crystal Structure of the Hemochromatosis Protein HFE and Characterization of Its Interaction with Transferrin Receptor", vol. 93, 111–123, Apr. 3, 1998.
Bjorkman et al., "The foreign antigen binding site and T cell recognition regions of class I histocompatibility antigens", Nature vol. 329, Oct. 8, 1987.
Fargion et al., "Genetic hemochromatosis in Italian patients with porphyria cutanea tarda", Journal of Hepatology 1996; 24:564–569.
Bulaj et al., "Clinical and Biochemical Abnormalities in People Heterozygous for Hemochromatosis", N.E. Journal of Medicine, Dec. 1996, vol. 335, No. 24, pp. 1799–1805.
Roberts et al. "The Frequency of Hemochromatosis–Associated Alleles Is Increased in British Patients With Sporadic Porphyria Cutanea Tarda", Hepatology vol. 25, No. 1, 1997, pp. 159–161.
Roberts et al, "Increased frequency of the haemochromatosis Cys282Tyr mutation in sporadic porphyria cutanea tarda", The lancet 1997; 349: 321–23.
O'Reilly et al., "Screening of Patients With Iron Overloan to Identify Hemochromatosis and Porphyria Cutanea Tarda", Arch Dermatol/vol. 133, Sep. 1997 pp. 1098–1101.
Sampietro et al., "High Prevalence of the His63Asp HPE Mutation in Italian Patients With Porphyria Cutanea Tarda", Hepatology vol. 27, No. 1, 1998.
Lefkowitch, MD, "Iron–Rich Foci in Chronic Viral Hepatitis", Human Pathology, vol. 29, No. 2 Feb. 1998 pp. 116–118.
Mark Worwood, "Revisiting various iron overload syndromes after the haemochromatosis gene discovery", Journal of Hepatology, 1998; 28: 26–27.
Stuart et al., "The C282Y mutation in the haemochromatosis gene (HFE) and hepatitis C virus infection are independent cofactors for porphyria . . . ", Jour. of Hepatology, 1998; 28: 404–409.
Bonkovsky et al., "Porphyria Cutanea Tarda, Hepatitis C, and HFE Gene Mutations in North America", Hepatology June 1998; vol. 27, No. 6, pp. 1661–1669.
Mendez et al., "Familial Porphyria Cutanea Tarda: Characterization of Seven Novel Uroporphyrinogen . . . ", Am. J. Hum. Genet. 63:1363–1375, 1998.
Agnes et al., "Strongly increased effeciency of altered peptide ligands by mannosylation", International Immunology, vol. 10, No. 9 pp. 1299–1304, 1998.
Wlater Gerhard, "Fusion of Cells in Suspension and Outgrowth of Hyrbids in Conditioned Medium", Plenum Press, Fusion Protocols, pp. 370–371, 1980.
Kohler et al., "Continuous cultures of fused cells secreting antibody of predefined specificity", Nature vol. 256, Aug. 7, 1975 pp. 495–497.

(List continued on next page.)

Primary Examiner—John S. Brusca
Assistant Examiner—Young Kim
(74) Attorney, Agent, or Firm—Ingrid A. Beattie; Mintz Levin Cohn Ferris Glovsky & Popeo

(57) ABSTRACT

The invention features a method of diagnosing an iron disorder, e.g., hemochroatosis, or a genetic susceptibility to developing such a disorder in a mammal by determining the presence of a mutation in exon 2 or in an intron of an HFE nucleic acid.

3 Claims, 3 Drawing Sheets

OTHER PUBLICATIONS

Ghose et al., "Strategy for Linkage of Cytotoxic Agents", Methods in Ezzymology, vol. 93, 1983. pp. 281–333.

Feder et al., "The Hemochromatosis Founder Mutation in HLA–H Disrupts . . . ", Journal of Biological Chemistry vol. 272, No. 22, pp. 14025–14028, 1997.

Edman et al., "Electric field directed nucleic acid hybridization on microchips", Nucleic Acids Research, 1997, vol. 25, No. 24, 1997.

Cheng et al., "Preparation and hybridization analysis of DNA/RNA from E. coli on microfabricated bioelectronic chips", Nature Biotechnology, vol. 16, No. 6, Jun. 1998, pp. 541–546.

Bernard et al., "Homogeneious Multiplex Genotyping of Hemochromatosis Mutation with Fluorscent Hybridization Probes", Americam Journal of Pathology, vol. 153, No. 4, 1998.

Nikiforov et al., Genetic Bit Analysis: a solid phase method for typing signle nucleotide polymorphisms Nucleic Acids Research, 1994, vol. 22, No. 2 4167–4175.

Rust et al., "Mutagenically separated PCR (MS–PCR) : a highly specific one step procedure for easy mutation detection", Nucleic Acids Research, 1993, vol. 21, No. 16 3623–3629.

Nickerson et al. "Automated DNA diagnostic using an ELISA–based oligonucleotide ligation assay", Proc. Natl. Acad. Sci. USA, vol. 87, pp. 8923–8927, 1990.

Clevers et al., "Mutations of the hereditary hemochromatosis candidate gene HLA–H in porphyria cutanea tarda" N. Engl. Med 1997 May 1;336(18):1327–8.

Sanchez et al., *Prevalence of the Cys282Tyr and His63Asp HFE gene mutations in Spanish patients with hereditary hemochromatosis and in controls*; Journal of Hepatology 1998; pp. 725–728.

Wenz et al.; *A rapid automated SSCP multiplex capillary electrophoresis protocol that detects the two common mutations implicated in hereditary hemochromatosis (HH)*; Hum. Genet., vol. 104, No. 1, 1999; pp. 29–35.

Bernard et al., *Homogeneous Multiplex Genotyping of Hemochromatosis Mutations with Fluorescent Hybridization Probes*, Am. J. Pathology, vol. 153, No. 4, Oct., 1998. pp. 1055–1061.

Mura et al., *HFE Mutations Analysis in 711 Hemochromatosis Probands: Evidence for S65C Implication In Mild Form of Hemochromatosis*; Blood, vol. 93, No. 8, 1999. pp. 2502–2505.

Barton et al., *Two Novel Missense Mutations of the HFE Gene (I105T and G93R) and Identification of the S65C Mutation in Alabama Hemochromatosis Probands*, Blood Cells, Molecules, and Diseases, vol. 25, No. 9, 1999. pp. 147–155.

SEQUENCE LISTING

<160> NUMBER OF SEQ ID NOS: 30

<210> SEQ ID NO 1
<211> LENGTH: 2506
<212> TYPE: DNA
<213> ORGANISM: Homo Sapiens
<220> FEATURE:
<221> NAME/KEY: mutation
<222> LOCATION: (0)...(0)
<223> OTHER INFORMATION: Missense mutation at nucleotide 314

<400> SEQUENCE: 1

| | | | | | |
|---|---|---|---|---|---|
| atgggcccgc | gagccaggcc | ggcgcttctc | ctcctgatgc | ttttgcagac | cgcggtcctg | 60 |
| cagggcgct | tgctgcgttc | acactctctg | cactacctct | tcatgggtgc | ctcagagcag | 120 |
| gaccttggtc | tttccttgtt | tgaagctttg | ggctacgtgg | atgaccagct | gttcgtgttc | 180 |
| tatgatcatg | agagtcgccg | tgtggagccc | cgaactccat | gggtttccag | tagaatttca | 240 |
| agccagatgt | ggctgcagct | gagtcagagt | ctgaaagggt | gggatcacat | gttcactgtt | 300 |
| gacttctgga | ctattatgga | aaatcacaac | cacagcaagg | agtcccacac | cctgcaggtc | 360 |
| atcctgggct | gtgaaatgca | agaagacaac | agtaccgagg | gctactggaa | gtacgggtat | 420 |
| gatgggcagg | accaccttga | attctgccct | gacacactgg | attggagagc | agcagaaccc | 480 |
| agggcctggc | ccaccaagct | ggagtgggaa | aggcacaaga | ttcgggccag | gcagaacagg | 540 |
| gcctacctgg | agagggactg | ccctgcacag | ctgcagcagt | tgctggagct | ggggagaggt | 600 |
| gttttggacc | aacaagtgcc | tcctttggtg | aaggtgacac | atcatgtgac | ctcttcagtg | 660 |
| accactctac | ggtgtcggc | cttgaactac | taccccccaga | acatcaccat | gaagtggctg | 720 |
| aaggataagc | agccaatgga | tgccaaggag | ttcgaaccta | agacgtatt | gcccaatggg | 780 |
| gatgggacct | accagggctg | ataaccttg | gctgtacccc | ctggggaaga | gcagagatat | 840 |
| acgtgccagg | tggagcaccc | aggcctggat | cagcccctca | ttgtgatctg | ggagccctca | 900 |
| ccgtctggca | ccctagtcat | tggagtcatc | agtggaattg | ctgttttttgt | cgtcatcttg | 960 |
| ttcattggaa | ttttgttcat | aatattaagg | aagaggcagg | gttcaagagg | agccatgggg | 1020 |
| cactacgtct | tagctgaacg | tgagtgacac | gcagcctgca | gactcactgt | gggaaggaga | 1080 |
| caaaactaga | gactcaaaga | gggagtgcat | ttatgagctc | ttcatgtttc | aggagagagt | 1140 |
| tgaacctaaa | catagaaatt | gcctgacgaa | ctccttgatt | ttagccttct | ctgttcattt | 1200 |
| cctcaaaaag | atttccccat | ttaggtttct | gagttcctgc | atgccggtga | tccctagctg | 1260 |
| tgacctctcc | cctggaactg | tctctcatga | acctcaagct | gcatctagag | gcttccttca | 1320 |
| tttcctccgt | cacctcagag | acatacacct | atgtcatttc | atttcctatt | tttggaagag | 1380 |
| gactccttaa | atttggggga | cttacatgat | tcattttaac | atctgagaaa | agctttgaac | 1440 |
| cctgggacgt | ggctagtcat | aaccttacca | gattttaca | catgtatcta | tgcattttct | 1500 |
| ggacccgttc | aactttttcct | ttgaatcctc | tctctgtgtt | acccagtaac | tcatctgtca | 1560 |
| ccaagccttg | gggattcttc | catctgattg | tgatgtgagt | tgcacagcta | tgaaggctgt | 1620 |
| gcactgcacg | aatggaagag | gcacctgtcc | cagaaaaagc | atcatggcta | tctgtgggta | 1680 |
| gtatgatggg | tgtttttagc | aggtaggagg | caaatatctt | gaaagggtt | gtgaagaggt | 1740 |
| gtttttctta | attggcatga | aggtgtcata | cagatttgca | agtttaatg | gtgccttcat | 1800 |
| ttgggatgct | actctagtat | tccagacctg | aagaatcaca | ataattttct | acctggtctc | 1860 |
| tccttgttct | gataatgaaa | attatgataa | ggatgataaa | agcacttact | tcgtgtccga | 1920 |
| ctcttctgag | cacctactta | catgcattac | tgcatgcact | tcttacaata | attctatgag | 1980 |
| ataggtacta | ttatccccat | ttcttttttta | aatgaagaaa | gtgaagtagg | ccgggcacgg | 2040 |
| tggctcgcgc | ctgtggtccc | aggtgctga | gattgcaggt | gtgagccacc | ctgcccagcc | 2100 |
| gtcaaaagag | tcttaatata | tatatccaga | tggcatgtgt | ttactttatg | ttactacatg | 2160 |
| cacttggctg | cataaatgtg | gtacaaccat | tctgtcttga | agggcaggtg | cttcaggata | 2220 |
| ccatatacag | ctcagaagtt | tcttctttag | gcattaaatt | ttagcaaaga | tatctcatct | 2280 |

-continued

```
cttcttttaa accattttct tttttgtgg ttagaaaagt tatgtagaaa aaagtaaatg    2340
tgatttacgc tcattgtaga aaagctataa aatgaataca attaaagctg ttatttaatt    2400
agccagtgaa aaactattaa caacttgtct attacctgtt agtattattg ttgcattaaa    2460
aatgcatata ctttaataaa tgtacattgt attgtaaaaa aaaaaa                  2506
```

<210> SEQ ID NO 2
<211> LENGTH: 348
<212> TYPE: PRT
<213> ORGANISM: Homo Sapiens

<400> SEQUENCE: 2

```
Met Gly Pro Arg Ala Arg Pro Ala Leu Leu Leu Met Leu Leu Gln
 1               5                  10                  15

Thr Ala Val Leu Gln Gly Arg Leu Leu Arg Ser His Ser Leu His Tyr
                20                  25                  30

Leu Phe Met Gly Ala Ser Glu Gln Asp Leu Gly Leu Ser Leu Phe Glu
            35                  40                  45

Ala Leu Gly Tyr Val Asp Asp Gln Leu Phe Val Phe Tyr Asp His Glu
        50                  55                  60

Ser Arg Arg Val Glu Pro Arg Thr Pro Trp Val Ser Ser Arg Ile Ser
65                  70                  75                  80

Ser Gln Met Trp Leu Gln Leu Ser Gln Ser Leu Lys Gly Trp Asp His
                85                  90                  95

Met Phe Thr Val Asp Phe Trp Thr Ile Met Glu Asn His Asn His Ser
            100                 105                 110

Lys Glu Ser His Thr Leu Gln Val Ile Leu Gly Cys Glu Met Gln Glu
        115                 120                 125

Asp Asn Ser Thr Glu Gly Tyr Trp Lys Tyr Gly Tyr Asp Gly Gln Asp
    130                 135                 140

His Leu Glu Phe Cys Pro Asp Thr Leu Asp Trp Arg Ala Ala Glu Pro
145                 150                 155                 160

Arg Ala Trp Pro Thr Lys Leu Glu Trp Glu Arg His Lys Ile Arg Ala
                165                 170                 175

Arg Gln Asn Arg Ala Tyr Leu Glu Arg Asp Cys Pro Ala Gln Leu Gln
            180                 185                 190

Gln Leu Leu Glu Leu Gly Arg Gly Val Leu Asp Gln Gln Val Pro Pro
        195                 200                 205

Leu Val Lys Val Thr His His Val Thr Ser Ser Val Thr Thr Leu Arg
    210                 215                 220

Cys Arg Ala Leu Asn Tyr Tyr Pro Gln Asn Ile Thr Met Lys Trp Leu
225                 230                 235                 240

Lys Asp Lys Gln Pro Met Asp Ala Lys Glu Phe Glu Pro Lys Asp Val
                245                 250                 255

Leu Pro Asn Gly Asp Gly Thr Tyr Gln Gly Trp Ile Thr Leu Ala Val
            260                 265                 270

Pro Pro Gly Glu Glu Gln Arg Tyr Thr Cys Gln Val Glu His Pro Gly
        275                 280                 285

Leu Asp Gln Pro Leu Ile Val Ile Trp Glu Pro Ser Pro Ser Gly Thr
    290                 295                 300

Leu Val Ile Gly Val Ile Ser Gly Ile Ala Val Phe Val Val Ile Leu
305                 310                 315                 320

Phe Ile Gly Ile Leu Phe Ile Ile Leu Arg Lys Arg Gln Gly Ser Arg
                325                 330                 335
```

```
Gly Ala Met Gly His Tyr Val Leu Ala Glu Arg Glu
        340                 345
```

<210> SEQ ID NO 3
<211> LENGTH: 23
<212> TYPE: DNA
<213> ORGANISM: Artificial Sequence
<220> FEATURE:
<223> OTHER INFORMATION: Primer

<400> SEQUENCE: 3
cctcctacta cacatggtta agg                                    23

<210> SEQ ID NO 4
<211> LENGTH: 21
<212> TYPE: DNA
<213> ORGANISM: Artificial Sequence
<220> FEATURE:
<223> OTHER INFORMATION: Reverse Primer

<400> SEQUENCE: 4
gctctgacaa cctcaggaag g                                      21

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
ggtggaaata gggacctatt cc                                     22

<210> SEQ ID NO 6
<211> LENGTH: 22
<212> TYPE: DNA
<213> ORGANISM: Artificial Sequence
<220> FEATURE:
<223> OTHER INFORMATION: Reverse Primer

<400> SEQUENCE: 6
cactctgcca ctagactata gg                                     22

<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7
gttccagtct tcctggcaag g                                      21

<210> SEQ ID NO 8
<211> LENGTH: 22
<212> TYPE: DNA
<213> ORGANISM: Artificial Sequence
<220> FEATURE:
<223> OTHER INFORMATION: Reverse Primer

<400> SEQUENCE: 8
aaatgcttcc catggatgcc ag                                     22

<210> SEQ ID NO 9
<211> LENGTH: 30
<212> TYPE: DNA

```
<213> ORGANISM: Artificial Sequence
<220> FEATURE:
<223> OTHER INFORMATION: Primer

<400> SEQUENCE: 9
aaaggatcca ccatgggccc gcgagccagg                                    30

<210> SEQ ID NO 10
<211> LENGTH: 20
<212> TYPE: DNA
<213> ORGANISM: Artificial Sequence
<220> FEATURE:
<223> OTHER INFORMATION: Reverse Primer

<400> SEQUENCE: 10
gtgagtctgc aggctgcgtg                                               20

<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11
gttccagtct tcctggcaag g                                             21

<210> SEQ ID NO 12
<211> LENGTH: 22
<212> TYPE: DNA
<213> ORGANISM: Artificial Sequence
<220> FEATURE:
<223> OTHER INFORMATION: Reverse Primer

<400> SEQUENCE: 12
aaatgcttcc catggatgcc ag                                            22

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
gttccagtct tcctggcaag g                                             21

<210> SEQ ID NO 14
<211> LENGTH: 22
<212> TYPE: DNA
<213> ORGANISM: Artificial Sequence
<220> FEATURE:
<223> OTHER INFORMATION: Reverse Primer

<400> SEQUENCE: 14
aaatgcttcc catggatgcc ag                                            22

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
gtgtggagcc tcaacatcct g                                             21
```

<210> SEQ ID NO 16
<211> LENGTH: 21
<212> TYPE: DNA
<213> ORGANISM: Artificial Sequence
<220> FEATURE:
<223> OTHER INFORMATION: Reverse Primer

<400> SEQUENCE: 16
acaagacctc agacttccag c                                          21

<210> SEQ ID NO 17
<211> LENGTH: 22
<212> TYPE: DNA
<213> ORGANISM: Artificial Sequence
<220> FEATURE:
<223> OTHER INFORMATION: Primer

<400> SEQUENCE: 17
ggtggaaata gggacctatt cc                                         22

<210> SEQ ID NO 18
<211> LENGTH: 22
<212> TYPE: DNA
<213> ORGANISM: Artificial Sequence
<220> FEATURE:
<223> OTHER INFORMATION: Reverse Primer

<400> SEQUENCE: 18
cactctgcca ctagagtata gg                                         22

<210> SEQ ID NO 19
<211> LENGTH: 21
<212> TYPE: DNA
<213> ORGANISM: Artificial Sequence
<220> FEATURE:
<223> OTHER INFORMATION: Primer

<400> SEQUENCE: 19
gttccagtct tcctggcaag g                                          21

<210> SEQ ID NO 20
<211> LENGTH: 21
<212> TYPE: DNA
<213> ORGANISM: Artificial Sequence
<220> FEATURE:
<223> OTHER INFORMATION: Reverse Primer

<400> SEQUENCE: 20
ttacctcctc aggcactcct c                                          21

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
aaaggatcca ccatgggccc gcgagccagg                                 30

<210> SEQ ID NO 22
<211> LENGTH: 20
<212> TYPE: DNA
<213> ORGANISM: Artificial Sequence
<220> FEATURE:

```
<223> OTHER INFORMATION: Reverse Primer

<400> SEQUENCE: 22
gtgagtctgc aggctgcgtg                                                    20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
tgcctgagga ggtaattatg g                                                  21

<210> SEQ ID NO 24
<211> LENGTH: 22
<212> TYPE: DNA
<213> ORGANISM: Artificial Sequence
<220> FEATURE:
<223> OTHER INFORMATION: Reverse Primer

<400> SEQUENCE: 24
aaatgcttcc catggatgcc ag                                                 22

<210> SEQ ID NO 25
<211> LENGTH: 21
<212> TYPE: DNA
<213> ORGANISM: Artificial Sequence
<220> FEATURE:
<223> OTHER INFORMATION: Primer

<400> SEQUENCE: 25
tgcctgagga ggtaattatg g                                                  21

<210> SEQ ID NO 26
<211> LENGTH: 22
<212> TYPE: DNA
<213> ORGANISM: Artificial Sequence
<220> FEATURE:
<223> OTHER INFORMATION: Reverse Primer

<400> SEQUENCE: 26
aaatgcttcc catggatgcc ag                                                 22

<210> SEQ ID NO 27
<211> LENGTH: 12146
<212> TYPE: DNA
<213> ORGANISM: Homo Sapiens

<400> SEQUENCE: 27
ggatccttta accgaggaga ttattatagc cggagctctg aagcagcaat ctcagttctt        60
gtgatagtga gcaaagaact acaaactaac accaaaatgc aagcttaaag caaagtttat       120
tgaagcacaa taatacactc tgagggacag cgggcttatt tctgcgaagt gaactcagca       180
cttctttaca gagctcaagg tgcttttatg gggtttgtgg ggaggagttg aggtttgggc       240
tgtatctgag tgacaggatg atgttatttg attgaagttt atagctatac aatctaaaat       300
taaactgtgc atggtcttac ctataatttg ttaagaaaag cctcccaggg atgggggggc       360
aaaactgtat gtaaattcta ttataatgat ggcatgatga acttgggtg aacttgaaga        420 caggcttttg tgttgttggg catgtgccac cttagggaat ttccacctgt accctccttt       480
ctctttctcc aggatatttt ggccacagac tttatcataa actccatccc ttagggtggc       540
```

```
attagggtag tcttgggcct gaatttaggt gggccagtgg ctgtcttagt gacagccttt     600
ccgctctctt ctgtcatccc ctcccaactg ctaatgtcta actacctaac aattacccat     660
taaatcagtg tgtctggggt taggagcagg cctcaatatg tttaatcatt ctccagataa     720
tcccaatact gtaaagtttg tgaaacactt gtcagataat tcaattatga aggctgtgga     780
acgtgtttca gtaggatcta attggttaat gttatgactt aattaatttg aatcaaaaaa     840
caaaatgaaa aagctttata tttctaagtc aaataagaca taagttggtc taaggttgag     900
ataaaatttt taaatgtatg attgaatttt gaaaatcata aatatttaaa tatctaaagt     960
tcagatcaga acattgcgaa gctactttcc ccaatcaaca acacccttc aggatttaaa    1020
aaccaagggg gacactggat cacctagtgt ttcacaagca ggtaccttct gctgtaggag    1080
agagagaact aaagttctga aagacctgtt gcttttcacc aggaagtttt actgggcatc    1140
tcctgagcct aggcaatagc tgtagggtga cttctggagc catccccgtt tccccgcccc    1200
ccaaaagaag cggagattta acggggacgt gcggccagag ctgggaaat gggcccgcga    1260
gccaggccgg cgcttctcct cctgatgctt ttgcagaccg cggtcctgca ggggcgcttg    1320
ctgcgtgagt ccgagggctg cgggcgaact aggggcgcgg cggggggtgga aaaatcgaaa    1380
ctagcttttt ctttgcgctt gggagtttgc taactttgga ggacctgctc aacccaatcc    1440
gcaagcccct ctccctactt tctgcgtcca gaccccgtga gggagtgcct accactgaac    1500
tgcagatagg ggtccctcgc cccaggacct gcccccctccc ccggctgtcc cggctctgcg    1560
gagtgacttt tggaaccgcc cactcccttc ccccaactag aatgcttta aataaatctc    1620
gtagttcctc acttgagctg agctaagcct ggggctcctt gaacctggaa ctcgggttta    1680
tttccaatgt cagctgtgca gttttttccc cagtcatctc caaacaggaa gttcttccct    1740
gagtgcttgc cgagaaggct gagcaaaccc acagcaggat ccgcacgggg tttccacctc    1800
agaacgaatg cgttgggcgg tgggggcgcg aaagagtggc gttgggatc tgaattcttc    1860
accattccac ccacttttgg tgagacctgg ggtggaggtc tctagggtgg gaggctcctg    1920
agagaggcct acctcgggcc tttccccact cttggcaatt gttcttttgc ctggaaaatt    1980
aagtatatgt tagtttttgaa cgtttgaact gaacaattct cttttcggct aggctttatt    2040
gatttgcaat gtgctgtgta attaagaggc ctctctacaa agtactgata tgaacatgt    2100
aagcaatgca ctcacttcta agttacattc atatctgatc ttatttgatt ttcactaggc    2160
ataggggaggt aggagctaat aatacgttta ttttactaga agtttaactgg aattcagatt    2220
atataactct tttcaggtta caaagaacat aaataatctg gttttctgat gttatttcaa    2280
gtactacagc tgcttctaat cttagttgac agtgattttg ccctgtagtg tagcacagtg    2340
ttctgtgggt cacacgccgg cctcagcaca gcactttgag ttttggtact acgtgtatcc    2400
acattttaca catgacaaga atgaggcatg gcacggcctg cttcctggca aatttattca    2460
atggtacacg gggctttggt ggcagagctc atgtctccac ttcatagcta tgattcttaa    2520
acatcacact gcattagagg ttgaataata aatttcatg ttgagcagaa atattcattg    2580
tttacaagtg taaatgagtc ccagccatgt gttgcactgt tcaagcccca agggagagag    2640
cagggaaaca agtctttacc ctttgatatt ttgcattcta gtgggagaga tgacaataag    2700
caaatgagca gaaagatata caacatcagg aaatcatggg tgttgtgaga agcagagaag    2760
tcagggcaag tcactctggg gctgacactt gagcagagac atgaaggaaa taagaatgat    2820
attgactggg agcagtattt cccaggcaaa ctgagtgggc ctggcaagtt ggattaaaaa    2880
```

```
gcgggttttc tcagcactac tcatgtgtgt gtgtgtgggg ggggggcgg cgtgggggtg      2940 ggaaggggga ctaccatctg catgtaggat gtctagcagt atcctgtcct ccctactcac      3000
taggtgctag gagcactccc ccagtcttga caaccaaaaa tgtctctaaa cttttgccaca     3060 tgtcacctag tagacaaact cctggttaag aagctcgggt tgaaaaaaat aaacaagtag     3120
tgctggggag tagaggccaa gaagtaggta atgggctcag aagaggagcc acaaacaagg     3180
ttgtgcaggc gcctgtaggc tgtggtgtga attctagcca aggagtaaca gtgatctgtc     3240
acaggctttt aaaagattgc tctggctgct atgtggaaag cagaatgaag ggagcaacag     3300
taaaagcagg gagcccagcc aggaagctgt tacacagtcc aggcaagagg tagtggagtg     3360
ggctgggtgg gaacagaaaa gggagtgaca aaccattgtc tcctgaatat attctgaagg     3420
aagttgctga aggattctat gttgtgtgag agaaagagaa gaattggctg ggtgtagtag     3480
ctcatgccaa ggaggaggcc aaggagagca gattcctgag ctcaggagtt caagaccagc     3540
ctgggcaaca cagcaaaacc ccttctctac aaaaaataca aaaattagct gggtgtggtg     3600
gcatgcacct gtgatcctag ctactcggga ggctgaggtg gagggtattg cttgagccca     3660
ggaagttgag gctgcagtga gccatgactg tgccactgta cttcagccta ggtgacagag     3720
caagaccctg tctcccctga cccctgaaa aagagaagag ttaaagttga ctttgttctt     3780
tattttaatt ttattggcct gagcagtggg gtaattggca atgccatttc tgagatggtg     3840
aaggcagagg aaagagcagt ttggggtaaa tcaaggatct gcatttggac atgttaagtt     3900
tgagattcca gtcaggcttc caagtggtga ggccacatag gcagttcagt gtaagaattc     3960
aggaccaagg cagggcacgg tggctcactt ctgtaatccc agcactttgg tggctgaggc     4020
aggtagatca tttgaggtca ggagtttgag acaagcttgg ccaacatggt gaaaccccat     4080
gtctactaaa aatacaaaaa ttagcctggt gtggtggcgc acgcctatag tcccaggttt     4140
tcaggaggct taggtaggag aatcccttga acccaggagg tgcaggttgc agtgagctga     4200
gattgtgcca ctgcactcca gcctgggtga tagagtgaga ctctgtctca aaaaaaaaa      4260 aaaaaaaaa aaaaaaaaa aactgaagga attattcctc aggatttggg tctaatttgc       4320
cctgagcacc aactcctgag ttcaactacc atggctagac acaccttaac attttctaga     4380
atccaccagc tttagtggag tctgtctaat catgagtatt ggaataggat ctgggggcag     4440 tgaggggtg gcagccacgt gtggcagaga aaagcacaca aggaaagagc acccaggact       4500
gtcatatgga agaaagacag gactgcaact caccccttcac aaaatgagga ccagacacag    4560
ctgatggtat gagttgatgc aggtgtgtgg agcctcaaca tcctgctccc ctcctactac     4620
acatggttaa ggcctgttgc tctgtctcca ggttcacact ctctgcacta cctcttcatg     4680
ggtgcctcag agcaggacct tggtcttttcc ttgtttgaag ctttgggcta cgtggatgac    4740
cagctgttcg tgttctatga tcatgagagt cgccgtgtgg agccccgaac tccatggggtt   4800 tccagtagaa tttcaagcca gatgtggctg cagctgagtc agagtctgaa agggtgggat    4860
cacatgttca ctgttgactt ctggactatt atggaaaatc acaaccacag caagggtatg    4920
tggagagggg gcctcacctt cctgaggttg tcagagcttt tcatcttttc atgcatcttg    4980
aaggaaacag ctggaagtct gaggtcttgt gggagcaggg aagagggaag gaatttgctt    5040
cctgagatca tttggtcctt ggggatggtg gaaataggga cctattcctt tggttgcagt    5100
taacaaggct ggggatttt ccagagtccc acacctgca ggtcatcctg ggctgtgaaa      5160
tgcaagaaga caacagtacc gagggctact ggaagtacgg gtatgatggg caggaccacc    5220
ttgaattctg ccctgacaca ctggattgga gagcagcaga acccagggcc tggcccacca    5280
```

```
agctggagtg ggaaaggcac aagattcggg ccaggcagaa cagggcctac ctggagaggg    5340
actgccctgc acagctgcag cagttgctgg agctggggag aggtgttttg gaccaacaag    5400
gtatggtgga aacacacttc tgcccctata ctctagtggc agagtggagg aggttgcagg    5460
gcacggaatc cctggttgga gtttcagagg tggctgaggc tgtgtgcctc tccaaattct    5520
gggaagggac tttctcaatc ctagagtctc taccttataa ttgagatgta tgagacagcc    5580
acaagtcatg ggtttaattt cttttctcca tgcatatggc tcaaagggaa gtgtctatgg    5640
cccttgcttt ttatttaacc aataatcttt tgtatattta tacctgttaa aaattcagaa    5700
atgtcaaggc cgggcacggt ggctcacccc tgtaatccca gcactttggg aggccgaggc    5760
gggtggtcac aaggtcagga gtttgagacc agcctgacca catggtgaaa cccgtctct    5820 aaaaaaatac aaaaattagc tggtcacagt catgcgcacc tgtagtccca gctaattgga    5880
aggctgaggc aggagcatcg cttgaacctg ggaagcggaa gttgcactga gccaagatcg    5940
cgccactgca ctccagccta ggcagcagag tgagactcca tcttaaaaaa aaaaaaaaaa    6000 aaaagagaa ttcagagatc tcagctatca tatgaatacc aggacaaaat atcaagtgag    6060
gccacttatc agagtagaag aatcctttag gttaaaagtt tctttcatag aacatagcaa    6120
taatcactga agctacctat cttacaagtc cgcttcttat aacaatgcct cctaggttga    6180
cccaggtgaa actgaccatc tgtattcaat cattttcaat gcacataaag gcaatttta    6240 tctatcagaa caaagaacat gggtaacaga tatgtatatt tacatgtgag gagaacaagc    6300
tgatctgact gctctccaag tgacactgtg ttagagtcca atcttaggac acaaaatggt    6360
gtctctcctg tagcttgttt ttttctgaaa agggtatttc cttcctccaa cctatagaag    6420
gaagtgaaag ttccagtctt cctggcaagg gtaaacagat cccctctcct catccttcct    6480
ctttcctgtc aagtgcctcc tttggtgaag gtgacacatc atgtgacctc ttcagtgacc    6540
actctacggt gtcgggcctt gaactactac ccccagaaca tcaccatgaa gtggctgaag    6600
gataagcagc caatggatgc caaggagttc gaacctaaag acgtattgcc caatggggat    6660
gggacctacc agggctggat aaccttggct gtaccccctg gggaagagca gagatatacg    6720
tgccaggtgg agcacccagg cctggatcag cccctcattg tgatctgggg tatgtgactg    6780
atgagagcca ggagctgaga aaatctattg ggggttgaga ggagtgcctg aggaggtaat    6840
tatggcagtg agatgaggat ctgctctttg ttaggggatg ggctgagggt ggcaatcaaa    6900
ggctttaact tgctttttct gttttagagc cctcaccgtc tggcacccta gtcattggag    6960
tcatcagtgg aattgctgtt tttgtcgtca tcttgttcat tggaattttg ttcataatat    7020
taaggaagag gcagggttca agtgagtagg aacaaggggg aagtctctta gtacctctgc    7080
cccagggcac agtgggaaga ggggcagagg ggatctggca tccatgggaa gcatttttct    7140
catttatatt ctttggggac accagcagct ccctgggaga cagaaataaa tggttctccc    7200
cagaatgaaa gtctctaatt caacaaacat cttcagagca cctactattt tgcaagagct    7260
gtttaaggta gtacagggc tttgaggttg agaagtcact gtggctattc tcagaaccca    7320
aatctggtag ggaatgaaat tgatagcaag taaatgtagt taaagaagac cccatgaggt    7380
cctaaagcag gcaggaagca aatgcttagg gtgtcaaagg aaagaatgat cacattcagc    7440
tggggatcaa gatagccttc tggatcttga aggagaagct ggattccatt aggtgaggtt    7500
gaagatgatg ggaggtctac acagacggag caaccatgcc aagtaggaga gtataagca    7560 tactgggaga ttagaaataa ttactgtacc ttaaccctga gtttgcttag ctatcactca    7620
```

```
ccaattatgc atttctaccc cctgaacatc tgtggtgtag ggaaaagaga atcagaaaga       7680
agccagctca tacagagtcc aagggtcttt tgggatattg ggttatgatc actggggtgt       7740
cattgaagga tcctaagaaa ggaggaccac gatctcccct tatatggtgaa tgtgttgtta     7800 agaagttaga tgagaggtga ggagaccagt tagaaagcca ataagcattt ccagatgaga       7860
gataatggtt cttgaaatcc aatagtgccc aggtctaaat tgagatgggt gaatgaggaa       7920
aataaggaag agagaagagg caagatggtg cctaggtttg tgatgcctct ttcctgggtc       7980
tcttgtctcc acaggaggag ccatgggggca ctacgtctta gctgaacgtg agtgacacgc     8040
agcctgcaga ctcactgtgg gaaggagaca aaactagaga ctcaaagagg gagtgcattt      8100
atgagctctt catgtttcag gagagagttg aacctaaaca tagaaattgc ctgacgaact      8160
ccttgatttt agccttctct gttcatttcc tcaaaaagat ttccccattt aggtttctga       8220
gttcctgcat gccggtgatc cctagctgtg acctctcccc tggaactgtc tctcatgaac      8280
ctcaagctgc atctagaggc ttccttcatt tcctccgtca cctcagagac atacacctat      8340
gtcatttcat ttcctatttt tggaagagga ctccttaaat ttgggggact acatgattc       8400 attttaacat ctgagaaaag ctttgaaccc tgggacgtgg ctagtcataa ccttaccaga      8460
tttttacaca tgtatctatg cattttctgg acccgttcaa cttttccttt gaatcctctc      8520
tctgtgttac ccagtaactc atctgtcacc aagccttggg gattcttcca tctgattgtg      8580
atgtgagttg cacagctatg aaggctgtac actgcacgaa tggaagaggc acctgtccca      8640
gaaaaagcat catggctatc tgtgggtagt atgatggtgt ttttttagcag gtaggaggca   8700 aatatcttga aagggttgt gaagaggtgt tttttctaat tggcatgaag gtgtcataca        8760
gatttgcaaa gtttaatggt gccttcattt gggatgctac tctagtattc cagacctgaa      8820
gaatcacaat aattttctac ctggtctctc cttgttctga taatgaaaat tatgataagg      8880
atgataaaag cacttacttc gtgtccgact cttctgagca cctacttaca tgcattactg      8940
catgcacttc ttacaataat tctatgagat aggtactatt atcccccattt ctttttttaaa    9000 tgaagaaagt gaagtaggcc gggcacggtg gctcacgcct gtaatcccag cactttggga      9060
ggccaaagcg ggtggatcac gaggtcagga gatcgagacc atcctggcta acatggtgaa      9120 acccccatctc taataaaaat acaaaaaatt agctgggcgt ggtggcagac gcctgtagtc     9180
ccagctactc ggaaggctga ggcaggagaa tggcatgaac ccaggaggca gagcttgcag      9240
tgagccgagt ttgcgccact gcactccagc ctaggtgaca gagtgagact ccatctcaaa      9300
aaaataaaaa taaaaataaa aaaatgaaaa aaaaagaaaa gtgaagtata gagtatctca      9360
tagtttgtca gtgatagaaa caggtttcaa actcagtcaa tctgaccgtt tgatacatct       9420
cagacaccac tacattcagt agtttagatg cctagaataa atagagaagg aaggagatgg      9480
ctcttctctt gtctcattgt gtttcttctg aatgagcttg aatcacatga aggggaacag      9540
cagaaaacaa ccaactgatc ctcagctgtc atgtttcctt taaaagtccc tgaaggaagg      9600
tcctggaatg tgactccctt gctcctctgt tgctctcttt ggcattcatt tctttggacc      9660
ctacgcaagg actgtaattg gtggggacag ctagtggccc tgctgggctt cacacacggt      9720
gtcctcccta ggccagtgcc tctggagtca gaactctggt ggtatttccc tcaatgaagt      9780
ggagtaagct ctctcatttt gagatggtat aatggaagcc accaagtggc ttagaggatg      9840
cccaggtcct tccatggagc cactgggggtt ccggtgcaca ttaaaaaaaa aatctaacca    9900
ggacattcag gaattgctag attctgggaa atcagttcac catgttcaaa agagtctttt      9960
tttttttttt gagactctat tgcccaggct ggagtgcaat ggcatgatct cggctcactg       10020
```

```
taacctctgc ctcccaggtt caagcgattc tcctgtctca gcctcccaag tagctgggat    10080
tacaggcgtg caccaccatg cccggctaat ttttgtattt ttagtagaga cagggtttca    10140
ccatgttggc caggctggtc tcgaactctc ctgacctcgt gatccgcctg cctcggcctc    10200
ccaaagtgct gagattacag gtgtgagcca ccctgcccag ccgtcaaaag agtcttaata    10260
tatatatcca gatggcatgt gtttacttta tgttactaca tgcacttggc tgcataaatg    10320
tggtacaagc attctgtctt gaagggcagg tgcttcagga taccatatac agctcagaag    10380
tttcttcttt aggcattaaa ttttagcaaa gatatctcat ctcttctttt aaaccatttt    10440 cttttttgt ggttagaaaa gttatgtaga aaaagtaaa tgtgatttac gctcattgta     10500
gaaaagctat aaaatgaata caattaaagc tgttatttaa ttagccagtg aaaaactatt    10560
aacaacttgt ctattacctg ttagtattat tgttgcatta aaaatgcata actttaata    10620 aatgtacatt gtattgtata ctgcatgatt ttattgaagt tcttgttcat cttgtgtata    10680
tacttaatcg ctttgtcatt ttggagacat ttattttgct tctaatttct ttacattttg    10740
tcttacggaa tattttcatt caactgtggt agccgaatta atcgtgtttc ttcactctag    10800
ggacattgtc gtctaagttg taagacattg gttatttac cagcaaacca ttctgaaagc     10860
atatgacaaa ttatttctct cttaatatct tactatactg aaagcagact gctataaggc    10920
ttcacttact cttctacctc ataaggaata tgttacaatt aatttattag gtaagcattt    10980
gttttatatt ggttttattt cacctgggct gagatttcaa gaaacacccc agtcttcaca    11040
gtaacacatt tcactaacac atttactaaa catcagcaac tgtggcctgt taattttttt    11100
aatagaaatt ttaagtcctc attttctttc ggtgtttttt aagcttaatt tttctggctt    11160
tattcataaa ttcttaaggt caactacatt tgaaaaatca aagacctgca ttttaaattc    11220
ttattcacct ctggcaaaac cattcacaaa ccatggtagt aaagagaagg gtgacacctg    11280
gtggccatag gtaaatgtac cacggtggtc cggtgaccag agatgcagcg ctgagggttt    11340
tcctgaaggt aaaggaataa agaatgggtg gaggggcgtg cactgaaat cacttgtaga     11400 gaaaagcccc tgaaatttg agaaaacaaa caagaaacta cttaccagct atttgaattg     11460
ctggaatcac aggccattgc tgagctgcct gaactgggaa cacaacagaa ggaaaacaaa    11520
ccactctgat aatcattgag tcaagtacag caggtgattg aggactgctg agaggtacag    11580
gccaaaattc ttatgttgta ttataataat gtcatcttat aatactgtca gtatttata    11640 aaacattctt cacaaactca cacacattta aaaacaaaac actgtctcta aaatccccaa    11700 attttttcata aactcagttt taaactaact tttttcaaa ccacaatctg atttaacaat     11760
gactatcatt taaatatttc tgactttcaa attaaagatt ttcacatgca ggctgatatt    11820
tgtaattgtg attctctctg taggctttgg gtataatgtg ttctttccct tttttgcatc    11880
agcgattaac ttctacactc taacatgtag aatgttacta caatattaaa gtattttgta    11940
tgacaatttt atttgaaagc ctaggatgcg ttgacatcct gcatgcattt attacttgat    12000
atgcatgcat tctggtatct caagcattct atttctgagt aattgtttaa ggtgtagaag    12060
agatagatat ggtggatttg gagttgatac ttatatattt tctatttctt ggatggatga    12120
atttgtacat taaaagtttt ccatgg                                         12146
```

<210> SEQ ID NO 28
<211> LENGTH: 17
<212> TYPE: DNA
<213> ORGANISM: Artificial Sequence
<220> FEATURE:

```
<223> OTHER INFORMATION: G93R Mutation

<400> SEQUENCE: 28
gtctgaaacg gtgggat                                                    17

<210> SEQ ID NO 29
<211> LENGTH: 18
<212> TYPE: DNA
<213> ORGANISM: Artificial Sequence
<220> FEATURE:
<223> OTHER INFORMATION: I105T Mutation

<400> SEQUENCE: 29
acttctggac tactatgg                                                   18

<210> SEQ ID NO 30
<211> LENGTH: 17
<212> TYPE: DNA
<213> ORGANISM: Artificial Sequence
<220> FEATURE:
<223> OTHER INFORMATION: S65C Mutation

<400> SEQUENCE: 30
atcatgagtg tcgccgt                                                    17
```

MUTATIONS ASSOCIATED WITH IRON DISORDERS

This application is a divisional of U.S. patent application Ser. No. 09/277,457, filed on Mar. 26, 1999, now U.S. Pat. No. 6,355,425 B1. The aforementioned application is explicitly incorporated herein by reference in its entirety and for all purposes.

BACKGROUND OF THE INVENTION

Hemochromatosis is the most common progressive (and sometimes fatal) genetic disease in people of European descent. Hemochromatosis is a disease state characterized by an inappropriate increase in intestinal iron absorption. The increase can result in deposition of iron in organs such as the liver, pancreas, heart, and pituitary. Such iron deposition can lead to tissue damage and functional impairment of the organs.

In some populations, 60–100% of cases are attributable to homozygosity for a missense mutation at C282Y in the Histocompatibility iron (Fe) loading (HFE) gene, a major histocompatibility (MHC) non-classical class I gene located on chromosome 6p. Some patients are compound heterozygotes for C282Y and another mutation at H63D.

SUMMARY OF THE INVENTION

The invention is based on the discovery of novel mutations which are associated with aberrant iron metabolims, absorption, or storage, or in advanced cases, clinical hemochromatosis. Accordingly, the invention features a method of diagnosing an iron disorder, e.g., hemochromatosis or a genetic susceptibility to developing such a disorder, in a mammal by determining the presence of a mutation in exon 2 of an HFE nucleic acid. The mutation is not a C→G missense mutation at position 187 of SEQ ID NO:1 which leads to a H63D substitution. The nucleic acid is an RNA or DNA molecule in a biological sample taken from the mammal, e.g. a human patient, to be tested. The presence of the mutation is indicative of the disorder or a genetic susceptibility to developing it. An iron disorder is characterized by an aberrant serum iron level, ferritin level, or percent saturation of transferrin compared to the level associated with a normal control individual. An iron overload disorder is characterized by abnormally high iron absorption compared to a normal control individual. Clinical hemochromatosis is defined by an elevated fasting transferrin saturation level of greater than 45% saturation.

For example, the mutation is a missense mutation at nucleotide 314 of SEQ ID NO:1 such as 314C which leads to the expression of mutant HFE gene product with amino acid substitution I105T. The I105T mutation is located in the α1 helix of the HFE protein and participates in a hydrophobic pocket (the "F" pocket). The alpha helix structure of the α1 domain spans residues S80 to N108, inclusive. The I105T mutation is associated with an iron overload disorder.

TABLE 1

Human HFE cDNA sequence

```
 atgggcccg cgagccaggc
cggcgcttct cctcctgatg cttttgcaga ccgcggtcct gcagggggcgc ttgctgcgtt
cacactctct gcactacctc ttcatgggtg cctcagagca ggaccttggt ctttccttgt
ttgaagcttt gggctacgtg gatgaccagc tgttcgtgtt ctatgatcat gagagtcgcc
                                                      H63D    S65C
gtgtggagcc ccgaactcca tgggtttcca gtagaatttc aagccagatg tggctgcagc
tgagtcagag tctgaaaggg tgggatcaca tgttcactgt tgacttctgg actattatgg
                 G93R                                         I105T
aaaatcacaa ccacagcaag gagtcccaca ccctgcaggt catcctgggc tgtgaaatgc
aagaagacaa cagtaccgag ggctactgga agtacgggta tgatgggcag gaccaccttg
aattctgccc tgacaactg gattggagag cagcagaacc cagggcctgg cccaccaagc
tggagtggga aaggcacaag attcgggcca ggcagaacag ggcctacctg gagagggact
gccctgcaca gctgcagcag ttgctggagc tggggagagg tgttttggac caacaagtgc
ctccttttgt gaaggtgaca catcatgtga cctcttcagt gaccactcta cggtgtcggg
ccttgaacta ctaccccag aacatcacca tgaagtggct gaaggataag cagccaatgg
atgccaagga gttcgaacct aaagacgtat tgcccaatgg ggatgggacc taccagggct
ggataacctt ggctgtaccc cctggggaag agcagagata tacgtgccag gtggagcacc
caggcctgga tcagccctc attgtgatct gggagccctc accgtctggc accctagtca
ttggagtcat cagtggaatt gctgtttttg tcgtcatctt gttcattgga attttgttca
taatattaag gaagaggcag ggttcaagag gagccatggg gcactacgtc ttagctgaac
gtgagtgaca cgcagcctgc agactcactg tgggaaggag acaaaactag agactcaaag
agggagtgca tttatgagct cttcatgttt caggagagag ttgaacctaa acatagaaat
tgcctgacga actccttgat tttagccttc tctgttcatt tcctcaaaaa gatttcccca
tttaggtttc tgagttcctg catgccggtg atccctagct gtgacctctc ccctggaact
gtctctcatg aacctcaagc tgcatctaga ggcttccttc atttcctccg tcacctcaga
gacatacacc tatgtcattt catttcctat ttttggaaga ggactcctta aatttggggg
acttacatga ttcattttaa catctgagaa aagctttgaa ccctgggacg tggctagtca
taaccttacc agatttttac acatgtatct atgcattttc tggacccgtt caactttttcc
tttgaatcct ctctctgtgt tacccagtaa ctcatctgtc accaagcctt ggggattctt
ccatctgatt gtgatgtgag ttgcacagct atgaaggctg tgcactgcac gaatggaaga
ggcacctgtc ccagaaaaag catcatggct atctgtgggt agtatgatgg gtgttttttag
caggtaggag gcaaatatct tgaaaggggt tgtgaagagg tgttttttct aattggcatg
aaggtgtcat acagatttgc aaagtttaat ggtgccttca tttgggatgc tactctagta
ttccagacct gaagaatcac aataattttc tacctggtct ctccttgttc tgataatgaa
aattatgata aggatgataa aagcacttac ttcgtgtccg actcttctga gcacctactt
acatgcatta ctgcatgcac ttcttacaat aattctatga gataggtact attatcccca
tttcttttttt aaatgaagaa agtgaagtag gccgggcacg gtggctcgcg cctgtggtcc
cagggtgctg agattgcagg tgtgagccac cctgcccagc cgtcaaaaga gtcttaatat
atatatccag atggcatgtg tttactttat gttactacat gcacttggct gcataaatgt
```

TABLE 1-continued

Human HFE cDNA sequence

```
ggtacaacca ttctgtcttg aagggcaggt gcttcaggat accatataca gctcagaagt
ttcttcttta ggcattaaat tttagcaaag atatctcatc tcttcttta aaccattttc
ttttttttgtg gttagaaaag ttatgtagaa aaaagtaaat gtgatttacg ctcattgtag
aaaagctata aatgaatac aattaaagct gttatttaat tagccagtga aaaactatta
acaacttgtc tattacctgt tagtattatt gttgcattaa aaatgcatat actttaataa
atgtacattg tattgtaaaa aaaaaaa
```

(SEQ ID NO:1; GENBANK® Accession No. U60319)

TABLE 2

Human HFE gene product

MGPRARPALLLLMLLQTAVLQG

<u>RLLRSHSLHYLFMGASEODLGLSLFEALGYVDDOLFVFYDHESRRVEPRTPWVSSRTSSQ</u>

<u>MWLOLSQSLKGWDHMFTVDFWTIMENHNHSKESHTLQVILGCEMQEDNSTEGYWKYGYDG</u>

<u>QDHLEFCPDTLDWRAAEPRAWPTKLEWERHKIRARQNRAYLERDCPAQLQQLLELGRGVL</u>

DQQVPPLVKVTHHVTSSVTTLRCRALAYYPQNITMKWLKDKQPMDAKEFEPKDVLPNGDG

TYQGWITLAVPPGEEQRYTCQVEHPGLDQPLIVIWEPSPSGTLVIGVISGIAVFVVILFI

GILFIILRKRQGSRGAMGHYVLAERE (SEQ ID NO: 2; GENBANK ® Accession

No. U60319)

Residues 1–22=leader sequence; α1 domain underlined; residues 63, 65, 93, and 105 indicated in bold type)

Other mutations include nucleotide 277 of SEQ ID NO: 1, e.g., 277C which leads to expression of mutant HFE gene product G93R and one at nucleotide 193 of SEQ ID NO: 1, e.g., 193T, which leads to expression of mutant HFE gene product S65C.

Any biological sample containing an HFE nucleic acid or gene product is suitable for the diagnostic methods described herein. For example, the biological sample to be analyzed is whole blood, cord blood, serum, saliva, buccal tissue, plasma, effusions, ascites, urine, stool, semen, liver tissue, kidney tissue, cervical tissue, cells in amniotic fluid, cerebrospinal fluid, hair or tears. Prenatal testing can be done using methods used in the art, e.g., amniocentesis or chorionic villa sampling. Preferably, the biological sample is one that can be non-invasively obtained, e.g., cells in saliva or from hair follicles.

The assay is also used to screen individuals prior to donating blood to blood banks and to test organ tissue, e.g., a donor liver, prior to transplantation into a recipient patient. Both donors and recipients are screened.

In some cases, a nucleic acid is amplified prior to detecting a mutation. The nucleic acid is amplified using a first oligonucleotide primer which is 5' to exon 2 and a second oligonucleotide primer is 3' to exon 2. To detect mutation at nucleotide 314 of SEQ ID NO: 1, a first oligonucleotide primer which is 5' to nucleotide 314 and a second oligonucleotide primer which is 3' to nucleotide 314 is used in a standard amplification procedure such as polymerase chain reaction (PCR). To amplify a nucleic acid containing nucleotide 277 of SEQ ID NO: 1, a first oligonucleotide primer which is 5'. to nucleotide 277 and a second oligonucleotide primer which is 3' to nucleotide 277 is used. Similarly, a nucleic acid containing nucleotide 193 of SEQ ID NO:1 is amplified using primers which flank that nucleotide. For example, for nucleotide 277, the first primer has a nucleotide sequence of SEQ ID NO: 3 and said second oligonucleotide primer has a nucleotide sequence of SEQ ID NO: 4, or the first primer has a nucleotide sequence of SEQ ID NO: 15 and said second oligonucleotide primer has a nucleotide sequence of SEQ ID NO: 16. Table 3, below, shows examples of primer pairs for amplification of nucleic acids in exons and introns of the HFE gene.

TABLE 3

I. PRIMERS USED FOR AMPLIFICATION

| Target DNA | Forward Primer | Reverse Primer |
| --- | --- | --- |
| Exon 2 | CCTCCTACTACACATGGTTAAGG (SEQ ID NO: 3) | GCTCTGACAACCTCAGGAAGG (SEQ ID NO: 4) |
| Exon 3 | GGTGGAAATAGGGACCTATTCC (SEQ ID NO: 5) | CACTCTGCCACTAGACTAT-AGG (SEQ ID NO: 6) |

TABLE 3-continued

I. PRIMERS USED FOR AMPLIFICATION

| Target DNA | Forward Primer | Reverse Primer |
|---|---|---|
| Exon 4 | GTTCCAGTCTTCCTGGCAAGG (SEQ ID NO: 7) | AAATGCTTCCCATGGATGC-CAG (SEQ ID NO: 8) |
| RT-PCR | AAAGGATCCACCATGGGCCCGCGAGCCAGG (SEQ ID NO: 9) | GTGAGTCTGCAGGCTGCGTG (SEQ ID NO: 10) |
| Intron 4 | GTTCCAGTCTTCCTGGCAAGG (SEQ ID NO: 11) | AAATGCTTCCCATGGATGC-CAG (SEQ ID NO: 12) |
| Intron 5 | GTTCCAGTCTTCCTGGCAAGG (SEQ ID NO: 13) | AAATGCTTCCCATGGATGC-CAG (SEQ ID NO: 14) |

II. PRIMERS USED FOR AMPLIFICATION

| Target DNA | Forward Primer | Reverse Primer |
|---|---|---|
| Exon 2 | GTGTGGAGCCTCAACATCCTG (SEQ ID NO: 15) | ACAAGACCTCAGACTTCCAGC (SEQ ID NO: 16) |
| Exon 3 | GGTGGAAATAGGGACCTATTCC (SEQ ID NO: 17) | CACTCTGCCACTAGAGTAT-AGG (SEQ ID NO: 18) |
| Exon 4 | GTTCCAGTCTTCCTGGCAAGG (SEQ ID NO: 19) | TTACCTCCTCAGGCACTCCTC (SEQ ID NO: 20) |
| RT-PCR | AAAGGATCCACCATGGGCCCGCGAGCCAGG (SEQ ID NO: 21) | GTGAGTCTGCAGGCTGCGTG (SEQ ID NO: 22) |
| Intron 4 | TGCCTGAGGAGGTAATTATGG (SEQ ID NO: 23) | AAATGCTTCCCATGGATGC-CAG (SEQ ID NO: 24) |
| Intron 5 | TGCCTGAGGAGGTAATTATGG (SEQ ID NO: 25) | AAATGCTTCCCATGGATGC-CAG (SEQ ID NO: 26) |

Mutations in introns of the HFE gene have now been associated with iron disorders and/or hemochromatosis. By "exon" is meant a segment of a gene the sequence of which is represented in a mature RNA product, and by "intron" is meant a segment of a gene the sequence of which is not represented in a mature RNA product. An intron is a part of a primary nuclear transcript which is subsequently spliced out to produce a mature RNA product, i.e., a mRNA, which is then transported to the cytoplasm. A method of diagnosing an iron disorder or a genetic susceptibility to developing the disorder is carried out by determining the presence or absence of a mutation in an intron of HFE genomic DNA in a biological sample. The presence of the mutation is indicative of the disorder or a genetic susceptibility to developing the disorder. The presence of a mutation in an intron is a marker for an exon mutation, e.g., a mutation in intron 4, e.g., at nucleotide 6884 of SEQ ID NO:27 is associated with the S65C mutation in exon 2. A mutation in intron 5, e.g., at nucleotide 7055 of SEQ ID NO:27 is associated with hemochromatosis. In some cases, intron mutations may adversely affect proper splicing of exons or may alter regulatory signals. Preferably, the intron 4 mutation is 6884C and the intron 5 mutation is 7055G. To amplify nucleic acid molecule containing nucleotide 6884 or 7055, primers which flank that nucleotide, e.g., those described in Table 3, are used according to standard methods. Nucleic acid-based diagnostic methods may or may not include a step of amplification to increase the number of copies of the nucleic acid to be analyzed. To detect a mutation in intron 4, a patient-derived nucleic acid may be amplified using a first oligonucleotide primer which is 5' to intron 4 and a second oligonucleotide primer which is 3' to intron 4, and to detect a mutation in intron 5, the nucleic acid may be amplified using a first oligonucleotide primer which is 5' to intron 5 and a second oligonucleotide primer which is 3' to intron 5 (see, e.g., Table 3).

In addition to nucleic acid-based diagnostic methods, the invention includes a method of diagnosing an iron overload disorder or a genetic susceptibility thereto by determining the presence of a mutation in a HFE gene product in a biological sample. For example, the mutation results in a decrease in intramolecular salt bridge formation in the mutant HFE gene product compared to salt bridge formation in a wild type HFE gene product. The mutation which affects salt bridge formation is at or proximal to residue 63 of SEQ ID NO:2, but is not amino acid substitution H63D. Preferably, the mutation is between residues 23–113, inclusive of SEQ ID NO:2 (Table 2), more preferably, it is between residues 90–100, inclusive, of SEQ ID NO:2, more preferably, it is between residues 58–68, inclusive, of SEQ ID NO:2, and most preferably, the mutation is amino acid substitution S65C. Alternatively, the mutation which affects salt bridge formation is a mutation, e.g., an amino acid substitution at residue 95 or proximal to residue 95 of SEQ ID NO:2. Preferably, the mutation is G93R. Such an HFE mutation is detected by immunoassay or any other ligand binding assay such as binding of the HFE gene product to a transferrin receptor. Mutations are also detected by amino acid sequencing, analysis of the structural conformation of the protein, or by altered binding to a carbohydrate or peptide mimetope.

A mutation indicative of an iron disorder or a genetic susceptibility to developing such a disorder is. located in the α1 helix (e.g., which spans residues 80–108, inclusive, of SEQ ID NO:2) of an HFE gene product. The mutation may be an addition, deletion, or substitution of an amino acid in the wild type sequence. For example, the mutant HFE gene product contains the amino acid substitution I105T or G93R or in the loop of the β sheet of the HFE molecule, e.g., mutation S65C.

Isolated nucleic acids encoding a mutated HFE gene products (and nucleic acids with nucleotide sequences complementary to such coding sequences) are also within the invention. Also included are nucleic acids which are at least 12 but less than 100 nucleotides in length. An isolated nucleic acid molecule is a nucleic acid molecule that is separated from the 5' and 3' sequences with which it is immediately contiguous in the naturally occurring genome of an organism. "Isolated" nucleic acid molecules include nucleic acid molecules which are not naturally occurring. For example, an isolated nucleic acid is one that has been amplified in vitro, e.g, by PCR; recombinantly produced; purified, e.g., by enzyme cleavage and gel separation; or chemically synthesized. For example, the restriction enzyme, Bst4C I (Sib Enzyme Limited, Novosibirsk, Russia), can be used to detect the G93R mutation (point mutation 277C); this enzyme cuts the mutated HFE nucleic acid but not the wild type HFE nucleic acid. Such nucleic acids are used as markers or probes for disease states. For example, a marker is a nucleic acid molecule containing a nucleotide polymorphism, e.g., a point mutation, associated with an iron disorder disease state flanked by wild type HFE sequences. The invention also encompasses nucleic acid molecules that hybridize, preferably under stringent conditions, to a nucleic acid molecule encoding a mutated HFE gene product (or a complementary strand of such a molecule). Preferably the hybridizing nucleic acid molecule is 400 nucleotides, more preferably 200 nucleotides, more preferably 100, more preferably 50, more preferably 25 nucleotides, more preferably 20 nucleotides, and most preferably 10–15 nucleotides, in length. For example, the nucleotide probe to detect a mutation is 13–15 nucleotides long. The nucleic acids are also used to produce recombinant peptides for generating antibodies specific for mutated HFE gene products. In preferred embodiments, an isolated nucleic acid molecule encodes an HFE polypeptide containing amino acid substitution I105T, G93R, or S65C, as well as nucleic acids the sequence of which are complementary to such nucleic acid which encode a mutant or wild type HFE gene product.

Also within the invention are substantially pure mutant HFE gene products, e.g., an HFE polypeptide containing amino acid substitution I105T, G93R, or S65C. Substantially pure or isolated HFE polypeptides include those that correspond to various functional domains of HFE or fragments thereof, e.g., a fragment of HFE that contains the α1 domain.

Wild type HFE binds to the transferrin receptor and regulates the affinity of transferrin receptor binding to transferrin. For example, a C282Y mutation in the HFE gene product reduces binding to the transferrin receptor, thus allowing the transferrin receptor to bind to transferrin (which leads to increased iron absorption).

The polypeptides of the invention encompass amino acid sequences that are substantially identical to the amino acid sequence shown in Table 2 (SEQ ID NO:2). Polypeptides of the invention are recombinantly produced, chemically synthesized, or purified from tissues in which they are naturally expressed according to standard biochemical methods of purification. Biologically active or functional polypeptides are those which possess one or more of the biological functions or activities of wild type HFE, e.g., binding to the transferrin receptor or regulation of binding of transferrin to the transferrin receptor. A functional polypeptide is also considered within the scope of the invention if it serves as an antigen for production of antibodies that specifically bind to an HFE epitope. In many cases, functional polypeptides retain one or more domains present in the naturally-occurring form of HFE.

The functional polypeptides may contain a primary amino acid sequence that has been altered from those disclosed herein. Preferably, the cysteine residues in exons 3 and 4 remain unchanged. Preferably the modifications consist of conservative amino acid substitutions. The terms "gene product", "protein", and is "polypeptide" are used herein to describe any chain of amino acids, regardless of length or post-translational modification (for example, glycosylation or phosphorylation). Thus, the term "HFE polypeptide or gene product" includes full-length, naturally occurring HFE protein, as well a recombinantly or synthetically produced polypeptide that correspond to a full-length naturally occurring HFE or to a particular domain or portion of it.

The term "purified" as used herein refers to a nucleic acid or peptide that is substantially free of cellular material, viral material, or culture medium when produced by recombinant DNA techniques, or chemical precursors or other chemicals when chemically synthesized. Polypeptides are said to be "substantially pure" when they are within preparations that are at least 60% by weight (dry weight) the compound of interest. Preferably, the preparation is at least 75%, more preferably at least 90%, and most preferably at least 99%, by weight the compound of interest. Purity can be measured by any appropriate standard method, for example, by column chromatography, polyacrylamide gel electrophoresis, or HPLC analysis.

Diagnostic kits for identifying individuals suffering from or at risk of developing an iron disorder are s also within the invention. A kit for detecting a nucleotide polymorphism associated with an iron disorder or a genetic susceptibility thereto contains an isolated nucleic acid which encodes at least a portion of the wild type or mutated HFE gene product, e.g., a portion which spans a mutation diagnostic for an iron disorder or hemochromatosis (or a nucleic acid the sequence of which is complementary to such a coding sequence). A kit for the detection of the presence of a mutation in exon 2 of an HFE nucleic acid contains a first oligonucleotide primer which is 5' to exon 2 and a second oligonucleotide primer is 3' to exon 2, and a kit for an antibody-based diagnostic assay includes an antibody which preferentially binds to an epitope of a mutant HFE gene product, e.g., an HFE polypeptide containing amino acid substitution I105T, G93R, or S65C, compared to its binding to the wild type HFE polypeptide. An increase in binding of the mutant HFE-specific antibody to a patient-derived sample (compared to the level of binding detected in a wild type sample or sample derived from a known normal control individual) indicates the presence of a mutation which is diagnostic of an iron disorder, i.e., that the patient from which the sample was taken has an iron disorder or is at risk of developing one. The kit may also contain an antibody which binds to an epitope of wild type HFE which contains residue 105, 93, or 65. In the latter case, reduced binding of the antibody to a patient-derived HFE gene product (compared to the binding to a wild type HFE gene product or a gene product derived from a normal control individual) indicates the presence of a mutation which is diagnostic of an iron disorder, i.e., that the patient from which the sample was taken has an iron disorder or is at risk of developing one.

Individual mutations and combinations of mutations in the HFE gene are associated with varying severity of iron disorders. For example, the C282Y mutation in exon 4 is typically associated with clinical hemochromatosis, whereas other HFE mutations or combinations of mutations in HFE nucleic acids are associated with disorders of varying prognosis. In some cases, hemochromatosis patients have been identified which do not have a C282Y mutation. The I105T and G93R mutations are each alone associated with an increased risk of iron overload (compared to, e.g., the H63D mutation alone), and the presence of both the I105T and H63D mutation is associated with hemochromatosis. Accordingly, the invention includes a method of determining the prognosis for hemochromatosis in a mammal suffering from or at risk of developing said hemochromatosis by (a) detecting the presence or absence of a first mutation in exon 4 in each allele of an HFE nucleic acid, e.g., patient-derived chromosomal DNA, and (b) detecting the presence of a second mutation in exon 2 in each allele of the nucleic acid. The presence of the first mutation in both chromosomes, i.e. an exon 4 homozygote such as a C282Y homozygote, indicates a more negative prognosis compared to the presence of the second mutation in one or both chromosomes, i.e., an exon 2 heterozygote or homozygote. An exon 4 mutation homozygote is also associated with a more negative prognosis compared to the presence of a first mutation (exon 4) in one allele and the presence of the second mutation (exon 2) in one allele, i.e., a compound heterozygote.

Other features and advantages of the invention will be apparent from the following detailed description, and from the claims.

DETAILED DESCRIPTION

Figure 1:
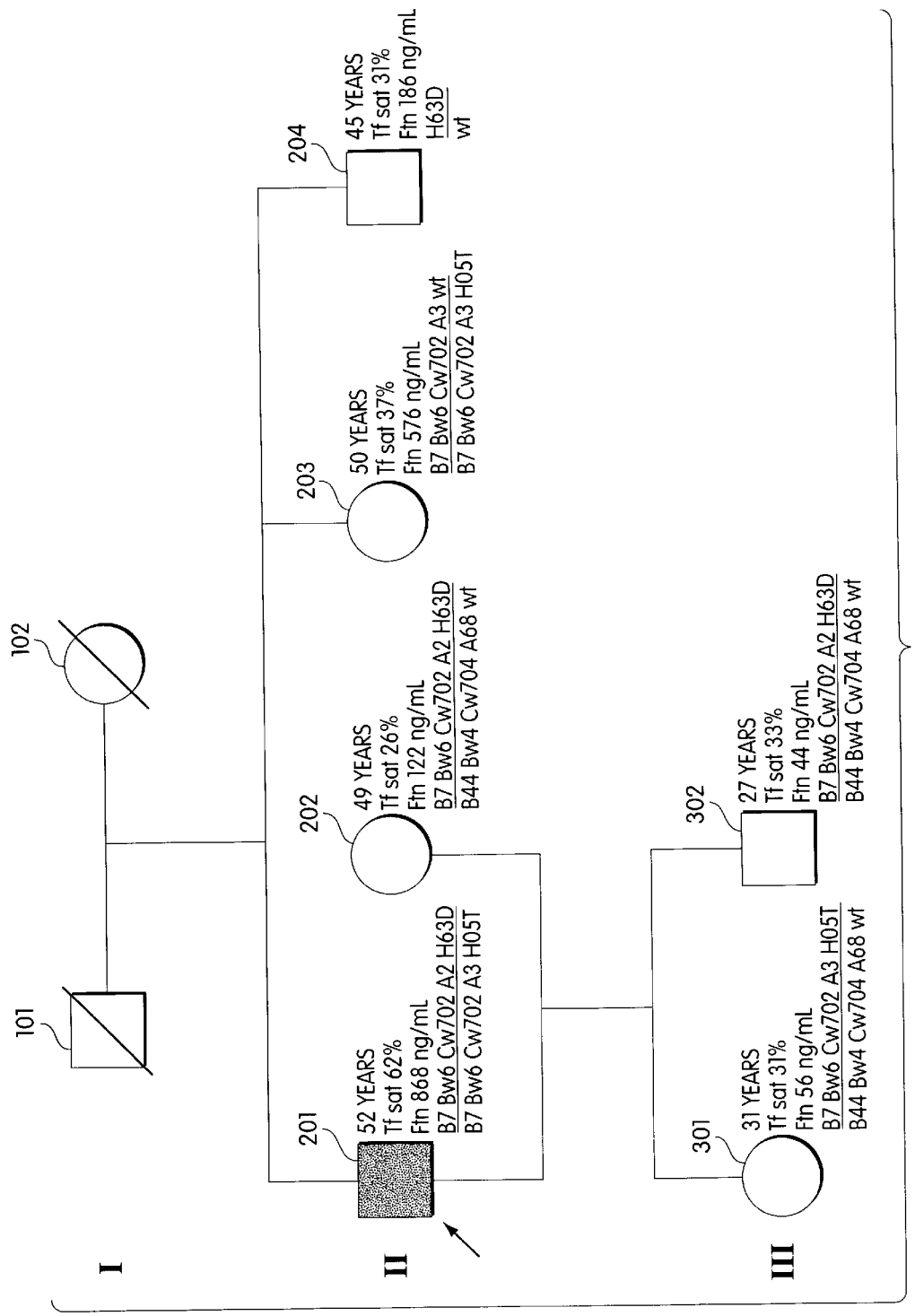
FIG. 1 is a diagram of the family of proband 1 (HFE genotype H63D/I105T). □=male, ●=female, ∅=deceased, ■=hemochromatosis phenotype. Proband 1 is indicated by an arrow. Phenotype and genotype data: age in year saturation; % Ftn=serum ferritin concentration. I105 separate chromosomes. The sister of the proband (II, 203) has hyperferritinemia.

A proband is the first individual in a family identified to be affected by hemochromatosis. Forward and reverse sequencing of HFE exons 2, 3, 4, and 5, and of portions of HFE introns 2, 4, and 5 was carried out on biological samples taken from twenty hemochromatosis probands who lacked C282Y homozygosity, C282Y/H63D compound heterozygosity, or H63D homozygosity. Four probands had novel HFE coding region mutations. Probands 1 and 2 were heterozygous for previously undescribed mutations: exon 2, nt 314T→C (314C; I105T), and exon 2, nt 277G→C (277C; G93R), respectively; these probands were also heterozygous for H63D and C282Y, respectively. Probands 3 and 4 were heterozygous for an HFE mutation in exon 2, nt 193A→T (193T; S65C). Twelve other probands did not have an exon 2 HFE exon mutation; four were heterozygous for H63D. In probands 1, 2, 3, and 4, the amino acid substitutions I105T, G93R, and S65C (respectively) occurred on separate chromosomes from those with the C282Y or H63D mutations. In 176 normal control subjects, two were heterozygous for S65C; I105T and G93R were not detected in controls. Nine probands were heterozygous and two probands were homozygous for a base-pair change at intron 2, nt 4919T/C (SEQ ID NO:27). Heterozygosity for a base-pair change in intron 4 (nt 6884T→C) was detected only in probands 3 and 4, both of whom also had S65C and HLA-A32. The intron 2 mutation is not diagnostic of an iron disorder and appears randomly in the population. One proband was heterozygous for a base-pair change at intron 5 (nt 7055A→G).

The data described herein indicate that, in addition to the C282Y and H63D HFE mutations, the HFE exon and intron 5 mutations described herein are diagnostic (and prognostic) of iron disorders.

Pathology of Iron Overload

Iron plays an essential role in normal growth and development, but in elevated concentrations, iron is a toxic inorganic molecule and is the leading cause of death in children by poisoning. It has been implicated in the pathophysiology of a number of common diseases, e.g., hepatitis, cancer, heart disease, reperfusion injury, rheumatoid arthritis, diabetes, AIDS, and psychological abnormalities (e.g. depression).

The incidence of cancer (especially liver cancer) rises dramatically in the course of hemochromatosis. Iron, acting alone or in synergy with other environmental agents, catalyzes free radical formation. These free radicals which mediate tissue damage also cause DNA double strand breaks and oncogene activation. Iron may also play a role in the pathogenesis of rheumatic diseases and in predisposition to heart disease. High levels of iron can also cause diabetes with 2% of diabetics being hemochromatosis patients. High levels of iron may also affect the disease progression of many viral diseases. Individuals infected with such viruses as hepatitis (e.g., hepatitis B or C) or HIV should be is tested for HFE mutations because of the impact increased iron stores have on the treatment and prognosis of such diseases.

Excessive iron stores and iron deposition is also a major contributing factor in the pathology and treatment of non-valvular heart disease. These conditions include dilated cardiomyopathy cased by deposition of iron in myocardial fibers; myocardial injury the product of anthracycline cardiomyopathy and re-perfusion injury. Increased iron stores may also be a contributing factor in myocardial infarction due to atherosclerosis. Some evidence suggests a significant increase in the incidence of reported heart disease in probands (cardiac symptoms—32%, insulin-dependent diabetes—18%, cardiac arrhythmia—17%, clinically significant coronary artery atherosclerosis—9%, and congestive heart failure—7%. Cardiac complications have been detected in 30% of patients. These include EKG abnormalities, congestive heart failure and cardiac arrhythmias. An increased frequency of HFE mutations in individuals with porphyria cutanea tarda indicates that HFE mutations may predispose an individual to developing this syndrome.

The effect of iron overload is irreparable damage to vital organs and a multiplicity of associated pathologies described above. The multiplicity of clinical symptoms (and associated pathologies) often causes misdiagnosis of hemochromatosis or failure to diagnose hemochromatosis.

Untreated hemochromatosis is characterized by iron overload of parenchymal cells, which is toxic and the probable cause of various complications including cirrhosis, and liver cancer, arthropathy, hypogonadotropic hypogonadism, marrow aplasia, skin disorders, diabetes mellitus, and cardiomyopathy. There are 1.5 to 2 million active cases in the U.S. of which 40% have progressive liver disease because they have not been properly diagnosed or treated.

In untreated hemochromatosis, iron is universally deposited in the hepatocytes of the liver. The iron is found primarily in the cytoplasm of hepatocytes, and by electron microscopy in lysosomal vacuoles, and in more severe cases iron has also been reported deposited in mitochondria. Other liver toxins such as alcohol, and hepatitis exacerbate the damage caused by the iron deposition. Patients with hemochromatosis are advised not to drink, because of increased liver damage, or to smoke, as iron deposition can also occur in the lungs.

Individuals which are homozygous (and to a lesser extent heterozygous) for an HFE mutation are at risk for developing increased levels of blood lead. Thus, it is important to identify heterozygous as well as homozygous patients.

Identification and detection of mutations in the HFE gene are critical to understanding the general mechanisms of iron disorders and diagnosing iron-related pathologies.

Nucleic Acid-based Assays for HFE Mutations

A biological sample containing RNA or DNA is obtained from an individual and the nucleic acid extracted. Optionally, the nucleic acid is amplified according to standard procedures such as PCR. A nucleic acid polymorphism, e.g, a single base pair polymorphism, is detected using methods well known in the art of molecular biology. For example, a mutation is detected using a standard sequencing assay, nucleic acid hybridization, e.g, using standard Southern, Northern, or dot blot hybridization assay systems and an HFE-specific oligonucleotide probe, is restriction enzyme fragment polymorphism analysis, oligonucleotide ligation assay (OLA; Nikerson et al., 1990, Nucl. Acids Res. 87:8923–8927), primer extension analysis (Nikiforov et al., 1994, Nucl. Acids Res. 22:4167–4175), single strand conformation polymorphism (SSCP) analysis, allele-specific PCR (Rust et al., 1993, Nucl. Acids Res. 6:3623–3629), denaturing gradient gel electrophoresis (DGGE), fluorescent probe melting curve analysis (Bernard et al., 1998, Am. J. Pathol. 153:1055–61), RNA mismatch cleavage assay, capillary hybridization, or TaqMan™ assay (PE Applied Biosystems, Foster City, Calif.). Nucleic acid hybridization assays are also carried out using a bioelectronic microchip technology known in the art, e.g., that described in Sosnowski et al., 1997, Proc. Natl. Acad. Sci. U.S.A. 94:1119–1123; Cheng et al. 1998, Nature Biotechnology 16:541–546; or Edman et al., 1997, Nucl. Acids Res. 25:4907–4914.

Detection of Mutations Using Antibodies and Other HFE Ligands

Anti-HFE antibodies are know in the art, e.g., those described by Feder et al., 1997, J. Biol. Chem. 272:14025–14028, or are obtained using standard techniques. Such antibodies can be polyclonal or monoclonal. Polyclonal antibodies can be obtained, for example, by the methods described in Ghose et al., Methods in Enzymology, Vol. 93, 326–327, 1983. An HFE polypeptide, or an antigenic fragment thereof, is used as an immunogen to stimulate the production of HFE-reactive polyclonal antibodies in the antisera of animals such as rabbits, goats, sheep, rodents and the like. HFE antibodies specific for mutated HFE gene products are raised by immunizing animals with a polypeptide spanning, the is mutation, e.g, a polypeptide which contains the mutations described herein. For example, the entire α1 domain of a mutant HFE gene product is used as an immunogen. Monoclonal antibodies are obtained by the process described by Milstein and Kohler in Nature, 256:495–97, 1975, or as modified by Gerhard, Monoclonal Antibodies, Plenum Press, 1980, pages 370–371. Hybridomas are screened to identify those producing antibodies that are highly specific for an HFE polypeptide containing a mutation characteristic of an iron metabolism abnormality or clinical hemochromatosis. Preferably, the antibody has an affinity of at least about $10^5$ liters/mole, preferably at least $10^6$ liters/mole, more preferably at least $10^8$ liters/mole, and most preferably, an affinity of at least about $10^9$ liters/mole.

Antibodies specific for the wild type HFE can also be used to diagnose hemochromatosis or iron metabolism abnormalities. Such antibodies are also useful research tools to identify novel mutations indicative of iron disorders or hemochromatosis. A reduction in binding to a wild type HFE-specific antibody indicates the presence of a mutation. Antibody binding is detected using known methods. For example, an ELISA assay involves coating a substrate, e.g., a plastic dish, with an antigen, e.g., a patient-derived biological sample containing an HFE gene product. An antibody preparation is then added to the well. Antibodies specific for a mutant HFE gene product bind or fail to bind to a patient-derived sample in the well. Non-binding material is washed away and a marker enzyme e.g., horse radish peroxidase or alkaline phosphatase, coupled to a second antibody directed against the antigen-specific primary antibody is added in excess and the nonadherent material is washed away. An enzyme substrate is added to the well and the enzyme catalyzed conversion is monitored as is indicative of presence of the mutation. Antibodies are also labelled with various sizes of colloidal gold particles or latex particles for detection of binding.

The invention employs not only intact monoclonal or polyclonal antibodies, but also an immunologically-active antibody fragment, for example, a Fab or (Fab)$_2$ fragment; an antibody heavy chain, an antibody light chain; a genetically engineered single-chain Fv molecule (Ladner et al., U.S. Pat. No. 4,946,778).

EXAMPLE 1

Selection and Characterization of Subjects

All individuals studied were Caucasians, 18 years of age or older, and from central Alabama. Twenty probands were identified that were either heterozygous for C282Y or H63D, or lacked these mutations. Hemochromatosis is typically diagnosed by detecting elevated saturation of transferrin, with elevated serum ferritin levels, combined with liver biopsy. Each proband patient described below was previously diagnosed to have hemochromatosis by the working diagnostic criterion for hemochromatosis of the American College of Pathologists (elevated fasting transferrin saturation of greater than 60% saturation for males and greater than 50% saturation for females) on at least two occasions in the absence of other known causes. Probands were interviewed regarding their general medical history, diet (including estimated iron content and ethanol consumption), medicinal iron use, receipt of blood transfusion, prior significant hemorrhage, blood donation for transfusion and/or therapeutic phlebotomy, and pregnancy and lactation. Each proband was also evaluated for viral hepatitis B and C and other hepatic disorders, excess ethanol intake, and hereditary, and acquired anemia. Iron overload was defined as evidence of systemic iron overload demonstrated by otherwise unexplained elevated serum ferritin concentration ($\geq 300$ ng/mL in men, $\geq 200$ ng/mL in women), increased hepatic iron content determined using hepatic biopsy specimens, or iron >4 g mobilized by phlebotomy. Complications of iron overload were evaluated and treated, and therapeutic phlebotomy was performed using standard methods. HFE mutation analysis for C282Y and H63D and human leukocyte antigen (HLA) immunophenotyping or molecular typing were performed using known methods. In some family members, HLA haplotyping had been performed previously for other disease associations, or their HLA type could be deduced from analysis of their kinship and HFE genotyping results. Measurement of serum iron and other clinical laboratory parameters and analysis of hepatic biopsy specimens were performed using routine methods. Control subjects (n=176) who were in apparently good health and were unrelated to the hemochromatosis probands were recruited from the general population. Iron parameters were measured and HLA typing was performed in two control subjects after HFE genotyping revealed that they had the S6SC mutation.

EXAMPLE 2

HFE Gene Analysis

PCR amplification was used to detect mutations. Genomic DNA was prepared from peripheral blood buffy coat or saliva using the QIAmpBlood Kit (QIAGEN, Valencia, Calif. ) or FTA Paper and FTA purification reagent (Fitzco Inc., Maple Plain, Minn.), respectively. Fragments were amplified from genomic DNA using eLONGase (Life Technologies, Gaithersburg, Md.) or HotStarTaq DNA polymerase (QIAGEN, Valencia, Calif.). Primers used to amplify each exon are shown in Table 3.

TABLE 4

| Human HFE genomic DNA |
| --- |

|  |  |  |  |  |  |
| ---: | --- | --- | --- | --- | --- |
| 1 | ggatccttta | accgaggaga | ttattatagc | cggagctctg | aagcagcaat ctcagttctt |
| 61 | gtgatagtga | gcaaagaact | acaaactaac | accaaaatgc | aagcttaaag caaagtttat |
| 121 | tgaagcacaa | taatacactc | tgagggacag | cgggcttatt | tctgcgaagt gaactcagca |
| 181 | cttctttaca | gagctcaagg | tgcttttatg | gggtttgtgg | ggaggagttg aggtttgggc |
| 241 | tgtatctgag | tgacaggatg | atgttatttg | attgaagttt | atagctatac aatctaaaat |
| 301 | taaactgtgc | atggtcttac | ctataatttg | ttaagaaaag | cctcccaggg atgggggggc |
| 361 | aaaactgtat | gtaaattcta | ttataatgat | ggcatgatga | acttggggtg aacttgaaga |
| 421 | caggcttttg | tgttgttggg | catgtgccac | cttagggaat | ttccacctgt accctccttt |
| 481 | ctctttctcc | aggatatttt | ggccacagac | tttatcataa | actccatccc ttagggtggc |
| 541 | attagggtag | tcttgggcct | gaatttaggt | gggccagtgg | ctgtcttagt gacagccttt |
| 601 | ccgctctctt | ctgtcatccc | ctcccaactg | ctaatgtcta | actacctaac aattacccat |
| 661 | taaatcagtg | tgtctggggt | taggagcagg | cctcaatatg | tttaatcatt ctccagataa |
| 721 | tcccaatact | gtaaagtttg | tgaaacactt | gtcagataat | tcaattatga aggctgtgga |
| 781 | acgtgtttca | gtaggatcta | attggttaat | gttatgactt | aattaatttg aatcaaaaaa |
| 841 | caaaatgaaa | aagctttata | tttctaagtc | aaataagaca | taagttggtc taaggttgag |
| 901 | ataaaatttt | taaatgtatg | attgaatttt | gaaaatcata | aatatttaaa tatctaaagt |
| 961 | tcagatcaga | acattgcgaa | gctactttcc | ccaatcaaca | acacccttc aggatttaaa |
| 1021 | aaccaagggg | gacactggat | cacctagtgt | ttcacaagca | ggtaccttct gctgtaggag |
| 1081 | agagagaact | aaagttctga | aagacctgtt | gcttttcacc | aggaagtttt acgggcac |
| 1141 | tcctgagcct | aggcaatagc | tgtagggtga | cttctggagc | catccccgtt tccccgcccc |
| 1201 | ccaaaagaag | cggagattta | acggggacgt | gcggccagag | ctggggaaat gggcccgcga |
| 1261 | gccaggccgg | cgcttctcct | cctgatgctt | ttgcagaccg | cggtcctgca ggggcgcttg |
| 1321 | ctgcgtgagt | ccgagggctg | cgggcgaact | aggggcgcgg | cgggggtgga aaaatcgaaa |
| 1381 | ctagcttttt | ctttgcgctt | gggagtttgc | taactttgga | ggacctgctc aacccaatcc |
| 1441 | gcaagcccct | ctccctactt | tctgcgtcca | gaccccgtga | gggagtgcct accactgaac |
| 1501 | tgcagatagg | ggtccctcgc | cccaggacct | gcccctccc | ccggctgtcc cggctctgcg |
| 1561 | gagtgacttt | tggaaccgcc | cactcccttc | ccccaactag | aatgcttta aataaatctc |
| 1621 | gtagttcctc | acttgagctg | agctaagcct | ggggctcctt | gaacctggaa ctcgggttta |

TABLE 4-continued

Human HFE genomic DNA

```
1681 tttccaatgt cagctgtgca gttttttccc cagtcatctc caaacaggaa
     gttcttccct
1741 gagtgcttgc cgagaaggct gagcaaaccc acagcaggat ccgcacgggg
     tttccacctc
1801 agaacgaatg cgttgggcgg tgggggcgcg aaagagtggc gttggggatc
     tgaattcttc
1861 accattccac ccacttttgg tgagacctgg ggtggaggtc tctagggtgg
     gaggctcctg
1921 agagaggcct acctcgggcc tttccccact cttggcaatt gttcttttgc
     ctggaaaatt
1981 aagtatatgt tagttttgaa cgtttgaact gaacaattct cttttcggct
     aggctttatt
2041 gatttgcaat gtgctgtgta attaagaggc ctctctacaa agtactgata
     atgaacatgt
2101 aagcaatgca ctcacttcta agttacattc atatctgatc ttatttgatt
     ttcactaggc
2161 atagggaggt aggagctaat aatacgttta ttttactaga agttaactgg
     aattcagatt
2221 atataactct tttcaggtta caaagaacat aaataatctg gttttctgat
     gttatttcaa
2281 gtactacagc tgcttctaat cttagttgac agtgattttg ccctgtagtg
     tagcacagtg
2341 ttctgtgggt cacacgccgg cctcagcaca gcactttgag ttttggtact
     acgtgtatcc
2401 acattttaca catgacaaga atgaggcatg gcacggcctg cttcctggca
     aatttattca
2461 atggtacacg gggctttggt ggcagagctc atgtctccac ttcatagcta
     tgattcttaa
2521 acatcacact gcattagagg ttgaataata aaatttcatg ttgagcagaa
     atattcattg
2581 tttacaagtg taaatgagtc ccagccatgt gttgcactgt tcaagcccca
     agggagagag
2641 cagggaaaca agtctttacc ctttgatatt ttgcattcta gtgggagaga
     tgacaataag
2701 caaatgagca gaaagatata caacatcagg aaatcatggg tgttgtgaga
     agcagagaag
2761 tcagggcaag tcactctggg gctgacactt gagcagagac atgaaggaaa
     taagaatgat
2821 attgactggg agcagtattt cccaggcaaa ctgagtgggc ctggcaagtt
     ggattaaaaa
2881 gcgggttttc tcagcactac tcatgtgtgt gtgtgtgggg ggggggcgg
     cgtggggtg
2941 ggaaggggga ctaccatctg catgtaggat gtctagcagt atcctgtcct
     ccctactcac
3001 taggtgctag gagcactccc ccagtcttga caaccaaaaa tgtctctaaa
     ctttgccaca
3061 tgtcacctag tagacaaact cctggttaag aagctcgggt tgaaaaaaat
     aaacaagtag
3121 tgctggggag tagaggccaa gaagtaggta atgggctcag aagaggagcc
     acaaacaagg
3181 ttgtgcaggc gcctgtaggc tgtggtgtga attctagcca aggagtaaca
     gtgatctgtc
3241 acaggctttt aaaagattgc tctggctgct atgtggaaag cagaatgaag
     ggagcaacag
3301 taaaagcagg gagcccagcc aggaagctgt tacacagtcc aggcaagagg
     tagtggagtg
3361 ggctgggtgg gaacagaaaa gggagtgaca aaccattgtc tcctgaatat
     attctgaagg
3421 aagttgctga aggattctat gttgtgtgag agaaagagaa gaattggctg
     ggtgtagtag
3481 ctcatgccaa ggaggaggcc aaggagagca gattcctgag ctcaggagtt
     caagaccagc
3541 ctgggcaaca cagcaaaacc ccttctctac aaaaaataca aaaattagct
     gggtgtggtg
3601 gcatgcacct gtgatcctag ctactcggga ggctgaggtg gagggtattg
     cttgagccca
3661 ggaagttgag gctgcagtga gccatgactg tgccactgta cttcagccta
     ggtgacagag
3721 caagaccctg tctcccctga ccccctgaaa aagagaagag ttaaagttga
     ctttgttctt
3781 tatttttaatt ttattggcct gagcagtggg gtaattggca atgccatttc
     tgagatggtg
3841 aaggcagagg aaagagcagt ttggggtaaa tcaaggatct gcatttggac
     atgttaagtt
3901 tgagattcca gtcaggcttc caagtggtga ggccacatag gcagttcagt
     gtaagaattc
```

TABLE 4-continued

Human HFE genomic DNA

```
3961 aggaccaagg cagggcacgg tggctcactt ctgtaatccc agcactttgg
     tggctgaggc
4021 aggtagatca tttgaggtca ggagtttgag acaagcttgg ccaacatggt
     gaaacccat
4081 gtctactaaa aatacaaaaa ttagcctggt gtggtggcgc acgcctatag
     tcccaggttt
4141 tcaggaggct taggtaggag aatcccttga acccaggagg tgcaggttgc
     agtgagctga
4201 gattgtgcca ctgcacctca gcctgggtga tagagtgaga ctctgtctca
     aaaaaaaaaa
4261 aaaaaaaaaa aaaaaaaaaa aactgaagga attattcctc aggatttggg
     tctaatttgc
4321 cctgagcacc aactcctgag ttcaactacc atggctagac acaccttaac
     attttctaga
4381 atccaccagc tttagtggag tctgtctaat catgagtatt ggaataggat
     ctgggggcag
4441 tgaggggtg gcagccacgt gtggcagaga aaagcacaca aggaaagagc
     acccaggact
4501 gtcatatgga agaaagacag gactgcaact caccccttcac aaaatgagga
     ccagacacag
4561 ctgatggtat gagttgatgc aggtgtgtgg agcctcaaca tcctgctccc
     ctcctactac
4621 acatggttaa ggcctgttgc tctgtctcca ggttcacact ctctgcacta
     cctcttcatg
4681 ggtgcctcag agcaggacct tggtctttcc ttgtttgaag ctttgggcta
     cgtggatgac
4741 cagctgttcg tgttctatga tcatgagagt cgccgtgtgg agccccgaac
     tccatgggtt
4801 tccagtagaa tttcaagcca gatgtggctg cagctgagtc agagtctgaa
     agggtgggat
4861 cacatgttca ctgttgactt ctggactatt atggaaaatc acaaccacag
     caagggtatg
4921 tggagagggg gcctcacctt cctgaggttg tcagagcttt tcatcttttc
     atgcatcttg
4981 aaggaaacag ctggaagtct gaggtcttgt gggagcaggg aagagggaag
     gaatttgctt
5041 cctgagatca tttggtcctt ggggatggtg gaaataggga cctattcctt
     tggttgcagt
5101 taacaaggct ggggattttt ccagagtccc acaccctgca ggtcatcctg
     ggctgtgaaa
5161 tgcaagaaga caacagtacc gagggctact ggaagtacgg gtatgatggg
     caggaccacc
5221 ttgaattctg ccctgacaca ctggattgga gagcagcaga acccagggcc
     tggcccacca
5281 agctggagtg ggaaaggcac aagattcggg ccaggcagaa cagggcctac
     ctggagaggg
5341 actgccctgc acagctgcag cagttgctgg agctggggag aggtgttttg
     gaccaacaag
5401 gtatggtgga aacacacttc tgcccctata ctctagtggc agagtggagg
     aggttgcagg
5461 gcacggaatc cctggttgga gtttcagagg tggctgaggc tgtgtgcctc
     tccaaattct
5521 gggaagggac tttctcaatc ctagagtctc taccttataa ttgagatgta
     tgagacagcc
5581 acaagtcatg ggtttaattt ctttttctcca tgcatatggc tcaaagggaa
     gtgtctatgg
5641 cccttgcttt ttatttaacc aataatcttt tgtatattta tacctgttaa
     aaatcagaa
5701 atgtcaaggc cgggcacggt ggctcacccc tgtaatccca gcactttggg
     aggccgaggc
5761 gggtggtcac aaggtcagga gtttgagacc agcctgacca acatggtgaa
     acccgtctct
5821 aaaaaaatac aaaaattagc tggtcacagt catgcgcacc tgtagtccca
     gctaattgga
5881 aggctgaggc aggagcatcg cttgaacctg ggaagcggaa gttgcactga
     gccaagatcg
5941 cgccactgca ctccagccta ggcagcagag tgagacccca tcttaaaaaa
     aaaaaaaaaa
6001 aaaagagaa ttcagagatc tcagctatca tatgaatacc aggacaaaat
     atcaagtgag
6061 gccacttatc agagtagaag aatcctttag gttaaaagtt tctttcatag
     aacatagcaa
6121 taatcactga agctaccttat cttacaagtc cgcttcttat aacaatgcct
     cctaggttga
6181 cccaggtgaa actgaccatc tgtattcaat cattttcaat gcactaaaag
     ggcaatttta
```

TABLE 4-continued

Human HFE genomic DNA

```
6241  tctatcagaa caaagaacat gggtaacaga tatgtatatt tacatgtgag
      gagaacaagc
6301  tgatctgact gctctccaag tgacactgtg ttagagtcca atcttaggac
      acaaaatggt
6361  gtctctcctg tagcttgttt ttttctgaaa agggtatttc cttcctccaa
      cctatagaag
6421  gaagtgaaag ttccagtctt cctggcaagg gtaaacagat cccctctcct
      catccttcct
6481  cttttcctgtc aagtgcctcc tttggtgaag gtgacacatc atgtgacctc
      ttcagtgacc
6541  actctacggt gtcgggcctt gaactactac ccccagaaca tcaccatgaa
      gtggctgaag
6601  gataagcagc caatggatgc caaggagttc gaacctaaag acgtattgcc
      caatgggat
6661  gggacctacc agggctggat aaccttggct gtaccccctg gggaagagca
      gagatatacg
6721  tgccaggtgg agcacccagg cctggatcag cccctcattg tgatctgggg
      tatgtgactg
6781  atgagagcca ggagctgaga aaatctattg ggggttgaga ggagtgcctg
      aggaggtaat
6841  tatggcagtg agatgaggat ctgctctttg ttaggggatg ggctgagggt
      ggcaatcaaa
6901  ggctttaact tgctttttct gttttagagc cctcaccgct tggcaccctaa
      gtcattggag
6961  tcatcagtgg aattcgtgtt ttgtcgtgca tcttgttcat tggaattttg
      ttcataatat
7021  taaggaagag gcagggttca agtgagtagg aacaaggggg aagtctctta
      gtacctctgc
7081  cccagggcac agtgggaaga ggggcagagg ggatctggca tccatgggaa
      gcatttttct
7141  catttatatt ctttggggac accagcagct ccctgggaga cagaaaataa
      tggttctccc
7201  cagaatgaaa gtctctaatt caacaaacat cttcagagca cctactattt
      tgcaagagct
7261  gtttaaggta gtacaggggc tttgaggttg agaagtcact gtggctattc
      tcagaaccca
7321  aatctggtag ggaatgaaat tgatagcaag taaatgtagt taaagaagac
      cccatgaggt
7381  cctaaagcag gcaggaagca aatgcttagg gtgtcaaagg aaagaatgat
      cacattcagc
7441  tggggatcaa gatagccttc tggatcttga aggagaagct ggattccatt
      aggtgaggtt
7501  gaagatgatg ggaggtctac acagacggag caaccatgcc aagtaggaga
      gtataaggca
7561  tactgggaga ttagaaataa ttactgtacc ttaaccctga gtttgcttag
      ctatcactca
7621  ccaattatgc atttctaccc cctgaacatc tgtggtgtag ggaaaagaga
      atcagaaaga
7681  agccagctca tacagagtcc aagggtcttt tgggatattg ggttatgatc
      actggggtgt
7741  cattgaagga tcctaagaaa ggaggaccac gatctccctt atatggtgaa
      tgtgttgtta
7801  agaagttaga tgagaggtga ggagaccagt tagaaagcca ataagcattt
      ccagatgaga
7861  gataatggtt cttgaaatcc aatagtgccc aggtctaaat tgagatgggt
      gaatgaggaa
7921  aataaggaag agagaagagg caagatggtg cctaggtttg tgatgcctct
      ttcctgggtc
7981  tcttgtctcc acaggaggag ccatggggca ctacgtctta gctgaacgtg
      agtgacacgc
8041  agcctgcaga ctcactgtgg gaaggagaca aaactagaga ctcaaagagg
      gagtgcattt
8101  atgagctctt catgtttcag gagagagttg aacctaaaca tagaaattgc
      ctgacgaact
8161  ccttgatttt agccttctct gttcatttcc tcaaaaagat ttccccattt
      aggtttctga
8221  gttcctgcat gccggtgatc cctagctgtg acctctcccc tggaactgtc
      tctcatgaac
8281  ctcaagctgc atctagaggc ttccttcatt tcctccgtca cctcagagac
      atacacctat
8341  gtcatttcat ttcctatttt tggaagagga ctccttaaat ttgggggact
      tacatgattc
8401  attttaacat ctgagaaaag ctttgaaccc tgggacgtgg ctagtcataa
      ccttaccaga
8461  ttttttacaca tgtatctatg cattttctgg acccgttcaa cttttccttt
      gaatcctctc
```

TABLE 4-continued

Human HFE genomic DNA

```
 8521 tctgtgttac ccagtaactc atctgtcacc aagccttggg gattcttcca
      tctgattgtg
 8581 atgtgagttg cacagctatg aaggctgtac actgcacgaa tggaagaggc
      acctgtccca
 8641 gaaaaagcat catggctatc tgtgggtagt atgatgggtg tttttagcag
      gtaggaggca
 8701 aatatcttga aaggggttgt gaagaggtgt tttttctaat tggcatgaag
      gtgtcataca
 8761 gatttgcaaa gtttaatggt gccttcattt gggatgctac tctagtattc
      cagacctgaa
 8821 gaatcacaat aattttctac ctggtctctc cttgttctga taatgaaaat
      tatgataagg
 8881 atgataaaag cacttacttc gtgtccgact cttctgagca cctacttaca
      tgcattactg
 8941 catgcacttc ttacaataat tctatgagat aggtactatt atccccattt
      cttttttaaa
 9001 tgaagaaagt gaagtaggcc gggcacggtg gctcacgcct gtaatcccag
      cactttggga
 9061 ggccaaagcg ggtggatcac gaggtcagga gatcgagacc atcctggcta
      acatggtgaa
 9121 accccatctc taataaaaat acaaaaaatt agctgggcgt ggtggcagac
      gcctgtagtc
 9181 ccagctactc ggaaggctga ggcaggagaa tggcatgaac ccaggaggca
      gagcttgcag
 9241 tgagccgagt ttgcgccact gcactccagc ctaggtgaca gagtgagact
      ccatctcaaa
 9301 aaaataaaaa taaaaataaa aaaatgaaaa aaaaaagaaa gtgaagtata
      gagtatctca
 9361 tagtttgtca gtgatagaaa caggtttcaa actcagtcaa tctgaccgtt
      tgatacatct
 9421 cagacaccac tacattcagt agtttagatg cctagaataa atagagaagg
      aaggagatgg
 9481 ctcttctctt gtctcattgt gtttcttctg aatgagcttg aatcacatga
      aggggaacag
 9541 cagaaaacaa ccaactgatc ctcagctgtc atgtttcctt taaaagtccc
      tgaaggaagg
 9601 tcctggaatg tgactccctt gctcctctgt tgctctcttt ggcattcatt
      tctttggacc
 9661 ctacgcaagg actgtaattg gtggggacag ctagtggccc tgctgggctt
      cacacacggt
 9721 gtcctcccta ggccagtgcc tctggagtca gaactctggt ggtatttccc
      tcaatgaagt
 9781 ggagtaagct ctctcatttt gagatggtat aatggaagcc accaagtggc
      ttagaggatg
 9841 cccaggtcct tccatggagc cactggggtt ccggtgcaca ttaaaaaaaa
      aatctaacca
 9901 ggacattcag gaattgctag attctgggaa atcagttcac catgttcaaa
      agagtctttt
 9961 ttttttttt gagactctat tgcccaggct ggagtgcaat ggcatgatct
      cggctcactg
10021 taacctctgc ctcccaggtt caagcgattc tcctgtctca gcctcccaag
      tagctgggat
10081 tacaggcgtg caccaccatg cccggctaat ttttgtattt ttagtagaga
      cagggtttca
10141 ccatgttggc caggctggtc tcgaactctc ctgacctcgt gatccgcctg
      cctcggcctc
10201 ccaaagtgct gagattacag gtgtgagcca ccctgcccag ccgtcaaaag
      agtcttaata
10261 tatatatcca gatggcatgt gtttacttta tgttactaca tgcacttggc
      tgcataaatg
10321 tggtacaagc attctgtctt gaagggcagg tgcttcagga taccatatac
      agctcagaag
10381 tttcttcttt aggcattaaa ttttagcaaa gatatctcat ctcttctttt
      aaaccatttt
10441 cttttttttgt ggttagaaaa gttatgtaga aaaagtaaa tgtgatttac
      gctcattgta
10501 gaaaagctat aaaatgaata caattaaagc tgttatttaa ttagccagtg
      aaaaactatt
10561 aacaacttgt ctattacctg ttagtattat tgttgcatta aaaatgcata
      tactttaata
10621 aatgtacatt gtattgtata ctgcatgatt ttattgaagt tcttgttcat
      cttgtgtata
10681 tacttaatcg ctttgtcatt ttggagacat ttattttgct tctaatttct
      ttacattttg
10741 tcttacggaa tattttcatt caactgtggt agccgaatta atcgtgtttc
      ttcactctag
```

TABLE 4-continued

Human HFE genomic DNA

```
10801  ggacattgtc gtctaagttg taagacattg gttattttac cagcaaacca
       ttctgaaagc
10861  atatgacaaa ttatttctct cttaatatct tactatactg aaagcagact
       gctataaggc
10921  ttcacttact cttctacctc ataaggaata tgttacaatt aatttattag
       gtaagcattt
10981  gttttatatt ggttttattt cacctgggct gagatttcaa gaaacacccc
       agtcttcaca
11041  gtaacacatt tcactaacac atttactaaa catcagcaac tgtggcctgt
       taattttttt
11101  aatagaaatt ttaagtcctc attttctttc ggtgtttttt aagcttaatt
       tttctggctt
11161  tattcataaa ttcttaaggt caactacatt tgaaaaatca aagacctgca
       ttttaaattc
11221  ttattcacct ctggcaaaac cattcacaaa ccatggtagt aaagagaagg
       gtgacacctg
11281  gtggccatag gtaaatgtac cacggtggtc cggtgaccag agatgcagcg
       ctgagggttt
11341  tcctgaaggt aaaggaataa agaatgggtg gagggcgtg cactggaaat
       cacttgtaga
11401  gaaaagcccc tgaaaatttg agaaaacaaa caagaaacta cttaccagct
       atttgaattg
11461  ctggaatcac aggccattgc tgagctgcct gaactgggaa cacaacagaa
       ggaaaacaaa
11521  ccactctgat aatcattgag tcaagtacag caggtgattg aggactgctg
       agaggtacag
11581  gccaaaattc ttatgttgta ttataataat gtcatcttat aatactgtca
       gtattttata
11641  aaacattctt cacaaactca cacacattta aaaacaaaac actgtctcta
       aaatccccaa
11701  atttttcata aactcagttt taaactaact tttttcaaa ccacaatctg
       atttaacaat
11761  gactatcatt taaatatttc tgactttcaa attaaagatt ttcacatgca
       ggctgatatt
11821  tgtaattgtg attctctctg taggctttgg gtataatgtg ttcttttcct
       tttttgcatc
11881  agcgattaac ttctacactc taacatgtag aatgttacta caatattaaa
       gtattttgta
11941  tgacaatttt atttgaaagc ctaggatgcg ttgacatcct gcatgcattt
       attacttgat
12001  atgcatgcat tctggtatct caagcattct atttctgagt aattgtttaa
       ggtgtagaag
12061  agatagatat ggtggatttg gagttgatac ttatatattt tctatttctt
       ggatggatga
12121  atttgtacat taaaagtttt ccatgg
```

(SEQ ID NO:27; GENBANK® Accession No. Z92910)

Exon 1 spans nt 1028–1324, inclusive; exon 2 spans nt 4652–4915, inclusive; exon 3 spans nt 5125–5400, inclusive; exon 4 spans nt 6494–6769, inclusive; exon 5 spans nt 6928–7041, inclusive; exon 6 spans nt 7995–9050, inclusive, and exon 7 spans nt 10206–10637, inclusive. Intron 4 spans nt 6770–6927, inclusive, and intron 5 spans nt 7042–7994, inclusive.

Total RNA for the RT-PCR was prepared from 1.5 mL of whole blood using the RNeasy Blood Kit (QIAGEN, Valencia, Calif.). Total messenger RNA encoding the HFE gene was transcribed and amplified with the primers shown above using standard methods, e.g., the Superscript ONE-STEP RT- PCR System (Life Technologies, Gaithersburg, Md.). The amplified product was directly subcloned into the pCR2.1-TOPO vector and transfected into TOP 10 bacteria (Invitrogen, Carlsbad, Calif.). Plasmid DNAs isolated from the subcloning were prepared with the UltraClean Mini Prep Kit (Mo Bio, Solana Beach, Calif.) and sequenced.

DNA sequencing was performed using the ABI Prism BigDye Terminator Cycle Sequencing Ready Reaction Kit (PE Applied Biosystems, Foster City, Calif.) and analyzed on an ABI Prism 377.

To detect mutations in exon 2 of the HFE gene, the genomic DNA of probands and normal control subjects were amplified and subjected to a dot blot hybridization assay. 1.0 µl of each resulting PCR product was then applied to a Magna Graph nylon membrane (MSI, Westboro, Mass.). The membranes were treated with 0.5 N NaOH/1.5 M NaCl to denature the DNA, neutralized with 0.5 M Tris-HCl (pH 8.0)/1.5 M NaCl, and rinsed with 2×SSC (1×SSC=0.15 M NaCl/0.015 M sodium citrate, pH 7.0). The DNAs were fixed on the membrane by UV irradiation using a Stratalinker 1800 (Stratagene, Inc., La Jolla, Calif.). The ECL 3'-oligolabelling and detection system (Amersham, Arlington Heights, Ill.) was used for synthesis of labeled oligonucleotide probes, hybridization, and signal detection. The oligonucleotide sequences used to detect each point mutation were (substituted bases are shown as upper case letters):

TABLE 5

| Oligonucleotide Probes | |
| --- | --- |
| Point Mutation | Oligonucleotide |
| G93R mutation | gtctgaaaCggtgggat (SEQ ID NO:28) |

TABLE 5-continued

Oligonucleotide Probes

| Point Mutation | Oligonucleotide |
|---|---|
| I105T mutation | acttctggactaCtatgg (SEQ ID NO:29) |
| S65C mutation | atcatgagTgtcgccgt (SEQ ID NO:30) |

For signal detection, each oligonucleotide was labeled with fluorescein-11-dUTP using terminal deoxynucleotidyl transferase according to the manufacturer's instructions (Amersham Ltd., Arlington Heights, Ill.). The membranes were prehybridized in 5×SSC, 0.1% Hybridization buffer component, 0.02% SDS, 5% LiquidBlock at 42° C. for approximately 2 hours. Labelled oligonucleotide probes were added to individual bags containing the membranes and prehybridization buffer and incubated at 42° C. overnight. The blots were washed twice with 5×SSC, 0.1 % SDS for 5 minutes at room temperature. Stringency washes for hybridization with oligonucleotides having the sequence of SEQ ID NO: 30 or 28 were performed twice in 0.2×SSC/0.1% SDS for 15 minutes at 42° C. Membranes probed with an oligonucleotide having the sequence of SEQ ID NO:29 was washed twice under less stringent conditions (0.5×SSC/0.1% SDS, 15 minutes at 42° C.). Detection of a fluorescent signal was performed according to standard methods.

EXAMPLES 3

Characterization of Probands

The mean age of the twenty probands was 44±11 years (range 27–62 years); thirteen (65.0%) were men and seven (35.0%) were women. Eleven had iron overload. One had hepatic cirrhosis, two had diabetes mellitus, four had arthropathy, and two had hypogonadotrophic hypogonadism. One proband also had hereditary stomatocytosis, another had beta-thalassemia trait, a third had ethanol intake >60 g daily, and a fourth had porphyria cutanea tarda. No proband had evidence of excess oral or parenteral iron intake, or of viral hepatitis B or C. At diagnosis of hemochromatosis, evaluation for common HFE mutations revealed that eleven probands were C282Y heterozygotes, five were H63D heterozygotes, and four did not inherit C282Y or H63D.

The mean age of the initial 176 control subjects was 52±15 years (range 18–86 years); 79 (44.9%) were men and 97 (55.1%) were women. There was no significant difference in the mean ages of men and women. Frequencies of HFE genotypes among the control subjects are shown in Table 6. These values are similar to those previously reported from normal persons from the same geographic area.

TABLE 6

Frequencies of HFE Genotypes in Alabama Subjects.

| HFE Genotype | Hemochromatosis Probands with "Atypical" HFE Genotypes, % (n) | Normal Control Subjects, % (n) |
|---|---|---|
| wt/wt | 15.00 (3) | 60.23 106) |
| C282Y/wt | 45.00 (9) | 13.06 (23) |
| H63D/wt | 20.00 (4) | 15.34 (27) |
| S65C/wt | 5.00 (1) | 1.14 (2) |
| C282Y/S65C | 5.00 (1) | 0 |
| C282Y/G93R | 5.00 (1) | 0 |

TABLE 6-continued

Frequencies of HFE Genotypes in Alabama Subjects.

| HFE Genotype | Hemochromatosis Probands with "Atypical" HFE Genotypes, % (n) | Normal Control Subjects, % (n) |
|---|---|---|
| H63D/I105T | 5.00 (1) | 0 |
| H63D/C282Y | 0 | 6.82 (12) |
| H63D/H63D | 0 | 3.41 (6) |

Results are expressed as percentage (n). The wild-type (wt) allele was defined as the HFE configuration in which the mutations C282Y, H63D, S65C, I105T, or G93R were not detected.

EXAMPLE 4

Identification of Novel HFE Mutations in Hemochromatosis Probands

Figure 2:
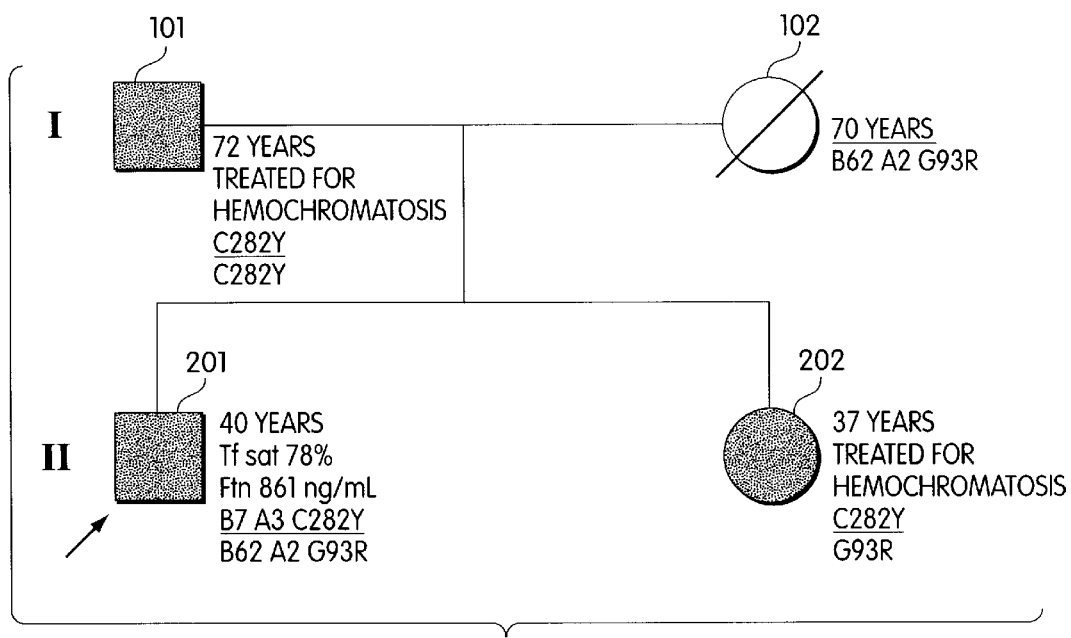
FIG. 2 is a diagram of the family of proband 2 (HFE genotype C282Y/G93R). Symbols and abbreviations are the same as those described for FIG. 1. Proband 2 is indicated with an arrow. G93R, C282Y, and wt alleles are known to exist only on separate chromosomes. The father and sister of the proband are being treated for hemochromatosis.

The following novel mutations (missense mutations) were identified in probands 1 and 2: exon 2, nt 314T→C (I105T), and exon 2, nt 277G→C (G93R), respectively (Table 7; FIGS. 1 and 2). Probands 3 and 4 had a S65C mutation The S65C mutation has been observed in hemochromatosis patients but has not been deemed to be indicative of a disease state. In contrast, the data presented herein indicate that the S65C mutation is diagnostic of a disease state. This result is surprising in view of earlier observations. Other than C282Y or H63D, no HFE exon mutations were detected in the remaining sixteen of the twenty probands (Table 6). Nine probands were heterozygous for a base-pair change at intron 2, nt 4919T/C (SEQ ID NO:27); two probands were homozygous for this base-pair change. Heterozygosity for a base-pair change in intron 4 (nt 6884T→C) was detected only in probands 3 and 4, both of whom also inherited S65C. One proband was heterozygous for a base-pair change at intron 5, nt 7055A→G.

Using dot blot methodology, heterozygosity for the S65C mutation was detected in two of 176 normal control subjects (Table 6). The G93R or I105T mutations were not detected in normal control subjects (Tables 6 and 8).

EXAMPLE 5

Association of Novel HFE Coding Region Mutations to C282Y and H63D and HFE Intron Alleles In proband 1, two mutations of exon 2 (H63D and I105T) were detected. After subcloning the genomic fragment, the subclones revealed that these mutations occurred on separate chromosomes; this observation was confirmed by family studies indicating segregation of I105T

TABLE 7

Phenotypes and Uncommon HFE Genotypes in Alabama Subjects*

| Subject† | Age (years), Sex | HFE Genotype | HLA Type | Transferrin Saturation, % | Serum Ferritin, ng/mL | Hepatocyte Iron Grade | Phlebotomy, Units |
|---|---|---|---|---|---|---|---|
| Proband 1 | 52 M | H63D/I105T | A2, 3; B7, 7 | 62 | 868 | 2+ | 20 |
| Proband 2‡ | 40 M | C282Y/G93R | A2, 3; B7, 62 | 78 | 861 | 4+ | 34 |
| Proband 3§ | 47 F | C282Y/S65C | A2, 32; B8, 44; Bw4, 6; Cw5, 7 | 90 | 281 | 3+ | 37 |
| Proband 4** | 81 F | S65C/wt | A2, 32; B14, 62 | 100 | 5,135 | N.D. | 37 |
| Normal Control 1 | 28 M | S65C/wt | A2, 31; B35, 60 | 28 | 141 | N.D. | N.D. |
| Normal Control 2 | 69 M | S65C/wt | A24, 26; B8, B37; Bw4, 6; Cw6, 5 (or 7) | 42 | 747 | 2+ | N.D. |

*Serum transferrin saturation, serum ferritin concentration, and percutaneous hepatic biopsy were performed before therapeutic phlebotomy was initiated. Reference ranges for these parameters are 15–45%; 20–300 ng/mL (men) and 20–200 ng/mL (women); and 0–1+, respectively. Iron depletion (serum ferritin ≦20 ng/mL) was induced by removing the indicated numbers of units of blood. None of these persons had evidence of hepatic cirrhosis, diabetes mellitus, hemochromatosis- associated arthropathy, hypogonadotrophic hypogonadism, other endocrinopathy, or cardiomyopathy. N.D. = not done. The mutations indicated are exon 4, nt 845G→A (C282Y); exon 2, nt 187C→G (H63D); exon 2, nt 314T→C (I105T); exon 2, nt 277G→C (G93R); and exon 2, nt 193A→T (S65C). The wild-type (wt) allele was defined as an HFE allele in which the mutations C282Y, H63D, S65C, I105T, or G93R were not detected.
† Countries of origin: Probands 1 and 2, England; Proband 3, Wales, England, and Americas (Cherokee); Proband 4, England and Ireland; Normal Control 1, England; Normal Control 2, The Netherlands.
‡ The father and sister of Proband 2 are presently undergoing therapy for hemochromatosis and iron overload, but their clinical and genetic data were unavailable.
§ Proband 3 had porphyria cutanea tarda alleviated with therapeutic phlebotomy.
**Proband 4 had hereditary atomatocytosis unaffected by phlebotomy treatments. 37 units of blood were removed by phlebotomy before treatment was discontinued due to stroke apparently unrelated to anemia or iron overload (post-treatment serum ferritin 1,561 ng/mL). Her 59 year-old daughter (who does not have hereditary atomatocytosis) had transferrin saturation 42%, serum ferritin 62 ng/mL, HLA type A1, 32; B14, 15; Bw4, 6; Cw3, 8, and HFE genotype S65C/H63D. These data permitted assignment of the S65C mutation in this family to a haplotype carrying HLA-A32; linkage of S65C and HLA-A32 was also observed in the family of Proband 3.

TABLE 8

Frequencies of HFE Alleles in Alabama Subjects.

| | wt * | C282Y | H63D | S65C† | I105T | G93R |
|---|---|---|---|---|---|---|
| Hemochromatosis Probands with "Atypical" HFE Genotypes (n = 20) | 0.500 | 0.275 | 0.125 | 0.050 | 0.025 | 0.025 |
| Normal Control Subjects (n = 176) | 0.750 | 0.099 | 0.145 | 0.006 | ‡ | ‡ |

The wild-type (wt) allele was defined as an HFE allele in which the mutations C282Y, H63D, S65C, I105T, or G93R were not detected.
† S65C was detected in 2 of 22 (0.091) proband chromosomes and in 2 of 266 (0.0075) control chromosomes that did not bear the C282Y, H63D, S65C, I105T, or G93R mutation.
‡ Based on this data set, the frequency of the I105T and G93R HFE alleles is estimated to be <0.0028, respectively.

and H63D (FIG. 1). In proband 2 (HFE genotype C282Y/G93R), RT-PCR analysis (with subsequent subcloning and sequencing) revealed that these HFE mutations occurred on separate chromosomes. Family studies of proband 3 (HFE genotype C282Y/S65C) indicated that the C282Y and S65C HFE alleles segregated independently, establishing their occurrence on separate chromosomes (Table 7, FIG. 3).

In proband 1 (HFE genotype H63D/I105T), the I105T mutation was co-inherited with HLA-A3, B7. In probands 3 and 4 and their respective families, S65C was inherited on the same chromosome as HLA-A32, indicating that HLA-A32 is a marker for chromosomes bearing the S65C mutation, and individuals with HLA-A32 have an increased risk for developing hemochromatosis. The G93R mutation is associated with HLA-A2, and individuals with that haplotype have an increased risk for developing hemochromatosis. The I105T mutation is associated with HLA-A3, e.g., HLA-A3, B7, and individuals with that haplotype have an increased risk for developing hemochromatosis. Among twenty probands tested, the nucleotide polymorphism in intron 4 (nt 6884T→C) was detected in probands 3 and 4, both of whom also had S65C. Subjects that tested positive for the S65C mutation all were found to have the intron 4 (6884T→C) mutation, including two probands (3 and 4), their families, and two normal controls.

EXAMPLE 6

HFE Coding Region Mutations and Clinical Phenotype

Figure 3:
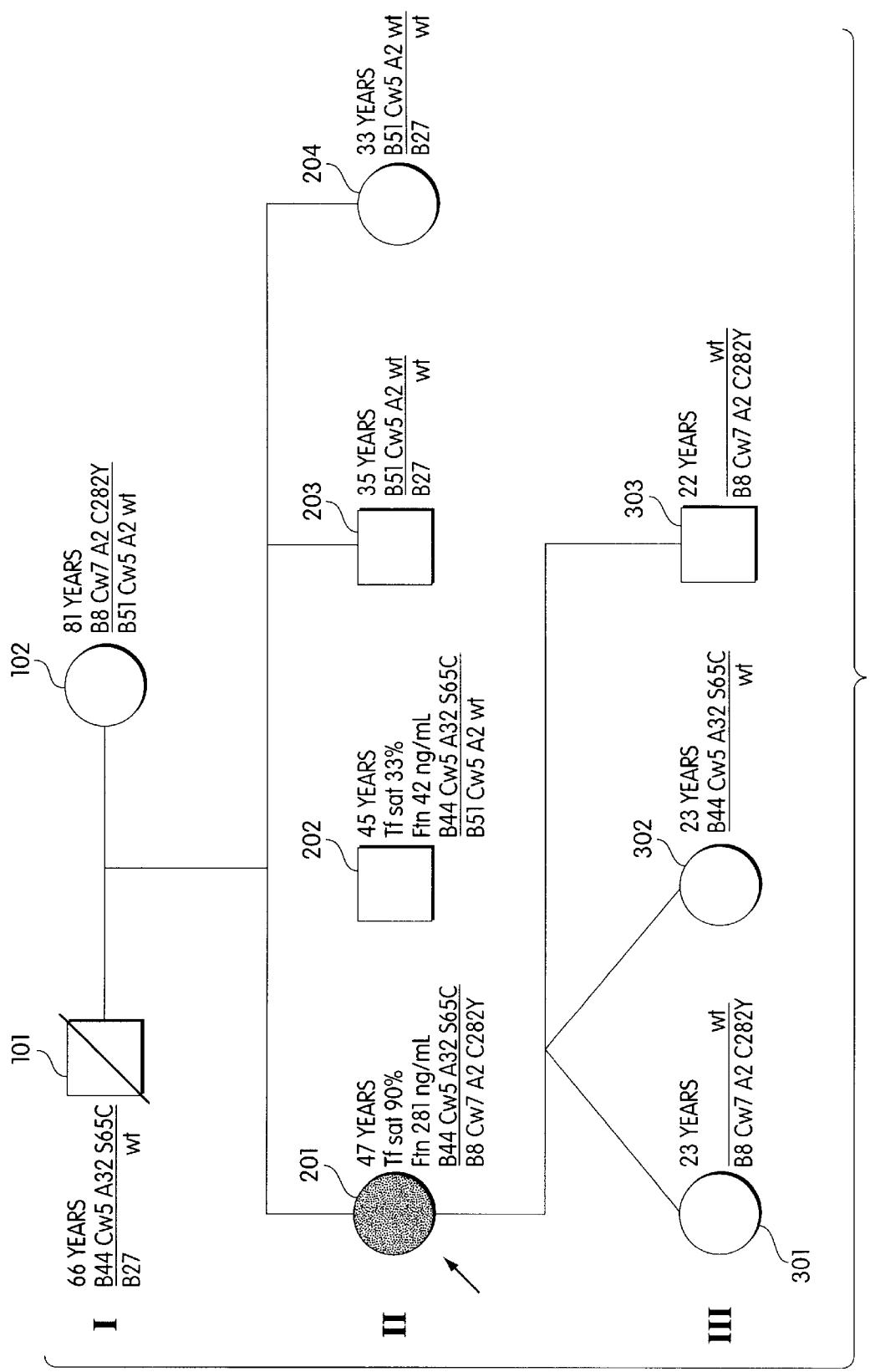
FIG. 3 is a diagram of the family of proband 3 (HFE genotype C282Y/S65C). Symbols and abbreviations are the same as those described for FIG. 1. Proband 3 is indicated with an arrow. S65C, C282Y, and wt alleles are know to exist only on separate chromosomes. Proband 3 also has porphyria cutanea tarda, and her brother (II, 203) has ankylosing spondylitis.

The I105T and G93R mutations were associated with a hemochromatosis clinical phenotype in probands 1 and 2 who also inherited H63D and C282Y, respectively. Proband 3 had clinical evidence of hemochromatosis, iron overload, and porphyria cutanea tarda associated with compound heterozygosity for C282Y and S65C. Proband 4 had severe iron overload associated with heterozygosity for S65C and co-inheritance of hereditary stomatocytosis (Table 7). The sister of proband 1 (HFE genotype I105T/wt) was not completely evaluated for hyperferritinemia (FIG. 1). Otherwise, family members of probands who were heterozygous for novel HFE mutations described herein had little or no evidence of abnormal iron parameters, a hemochromatosis phenotype, or of iron overload (Table 7 and 9; FIGS. 1 and 3). Normal Control 1 who had HFE genotype S65C/wt had a

TABLE 9

Hemochromatiosis (HC) Family study/patent

| Subject/Age/Sex | HLA Type | exon 2 | exon 4 | intron 4 5636bp | Tf sat** % | Ftn** ng/ml | Diagnosis/Hepatocyte Iron grade |
|---|---|---|---|---|---|---|---|
| Proband 1/57 M (201) | A2, 3; B7, 7 | H63D/H, I105T/1 | Wt | T | 62 | 868 | HC/2+ |
| brother/45 M (204) |  | H63D/H | Wt | T* | 31 | 186 |  |
| sister/50 F (203) | A3, 3; B7, 7 | I105T | Wt* | T* | 37 | 576 |  |
| daughter/31 F (301) | A32, 68; B7, 44 | I105T/1 | Wt* | T* | 31 | 56 |  |
| son/27 M (302) | A2, 68; B7, 44 | H63D/H | Wt% | T* | 33 | 44 |  |
| Proband 2/40 M | A2, 3; B7, 62 | G93R/G | C282Y/C | T | 78 | 861 | HC/4+ |
| Father |  | Wt | C282Y/Y* | T* |  |  | HC |
| Sister |  | G93R/G | C282Y/C* | T* |  |  | HC |
| Proband 3/47 (201) | A2, 32; B8, 44 | S65C/S | C282Y/C | T/C | 90 | 281 | HC/3+ |
| brother/45 M (202) | A2, 32; B44, 51 | S65C/S | Wt | T/C | 33 | 42 |  |
| mother/81 F (102) | A2, 2; B8, 51 | Wt | C282Y/C | T* | NT | NT |  |
| sister/33 F (204) | A2, 7; B27, 51 | Wt | Wt | T* | NT | NT |  |
| brother/35 M (203) | A2, 7; B27, 51 | Wt | Wt* | T* | NT | NT |  |
| sister |  | Wt | C282Y/C* | T* |  |  |  |
| sister |  | S65C/S | Wt* | T/C* |  |  |  |
| Proband 4/81 F | A2, 32; B14, 62 | S65C/S | Wt | T/C | 100 | S135 | HC + stomatocytosis |
| daughter/59* | A1, 32; B14, 15 | H63D/H, S65C/S | Wt* | T/C | 42 | 62 |  |
| Control 1/28 M | A2, 31; B35, 60 | S65C/S | Wt | T/C | 28 | 141 |  |
| Control 2/69 M | A24, 26; B8, 37 | S65C/S | Wt | T/C | 42 | 747 | 2+ |

*RE cut
**normal (15–45%)
***20–300 ng/ml (men)
2C–200 ng/ml (women)

normal iron phenotype (Table 7). Normal Control 2, who also had the HFE genotype S65C/wt, had hyperferritinemia and mildly increased stainable hepatocellular iron deposition, but had no symptoms or other objective findings attributable to iron overload (Table 7). These data indicate that S65C heterozygosity is associated with abnormal iron parameters.

EXAMPLE 7

HLA Gene Linkage

In the family of proband 1, the I105T mutation was linked to HLA-A3, B7, markers which are often linked to the C282Y mutation and its ancestral haplotype. HLA-A3, B7 is also significantly more common among C282Y-negative hemochromatosis probands than in normal control subjects tested. S65C was linked to HLA-A32 in probands 3 and 4 (and their respective families). The base-pair change in intron 4 (nt 6884T→C) was detected only in probands who inherited the S65C mutation. These data indicate that an intron 4 mutation (nt 6884→C) is a marker for chromosomes bearing the S65C HFE allele. Three of four probands who inherited mutated HFE exon 2 mutations described herein also inherited the C282Y or H63D mutations on separate chromosomes. In a fourth proband, the co-inheritance of S65C heterozygosity and hereditary stomatocytosis was associated with severe iron overload.

Altered interactions of transferrin receptor, transferrin, and C282Y and H63D mutant HFE protein contribute to the pathology of hemochromatosis. The S65C, G93R, and I105T mutations are located within the α1 domain: in the α1 helix of the HFE class I-like heavy chain (I105T and G93R), and at the tip of the A chain loop of the β-pleated sheet (S65C). These mutations affect the overall structure of the HFE gene product, and specifically affect the salt bridge between residues H63 and D95. The I105T substitution also inhibits proper folding of the α1 domain of the HFE gene product, and specifically affects the hydrophobicity of the hydrophobic F pocket.

Other embodiments are within the following claims.

What is claimed is:

1. A substantially pure HFE polypeptide comprising amino acid substitution I105T.

2. A substantially pure HFE polypeptide comprising amino acid substitution G93R.

3. A substantially pure HFE polypeptide comprising amino acid substitution S65C.

* * * * *